(12) United States Patent
Topolev

(10) Patent No.: US 11,471,371 B2
(45) Date of Patent: *Oct. 18, 2022

(54) MASSAGE DEVICE HAVING ELEMENT THAT STRAIGHTENS, METHOD FOR USE THEREOF, AND METHOD FOR MANUFACTURE THEREOF

(71) Applicant: Sergey Evgenievich Topolev, St. Petersburg (RU)

(72) Inventor: Sergey Evgenievich Topolev, St. Petersburg (RU)

(*) Notice: Subject to any disclaimer, the term of this patent is extended or adjusted under 35 U.S.C. 154(b) by 313 days.

This patent is subject to a terminal disclaimer.

(21) Appl. No.: 16/633,857

(22) PCT Filed: Jul. 27, 2018

(86) PCT No.: PCT/RU2018/050086
§ 371 (c)(1),
(2) Date: Jan. 24, 2020

(87) PCT Pub. No.: WO2019/022649
PCT Pub. Date: Jan. 31, 2019

(65) Prior Publication Data
US 2020/0163826 A1 May 28, 2020

(30) Foreign Application Priority Data
Jul. 27, 2017 (RU) .......................... RU2017126944

(51) Int. Cl.
*A61H 19/00* (2006.01)
*A61H 23/02* (2006.01)
*A61N 1/36* (2006.01)

(52) U.S. Cl.
CPC ......... *A61H 19/44* (2013.01); *A61H 23/0218* (2013.01); *A61H 23/0263* (2013.01);
(Continued)

(58) Field of Classification Search
CPC ........ A61H 7/00–005; A61H 2007/009; A61H 19/00–50; A61H 23/00; A61H 23/004;
(Continued)

(56) References Cited

U.S. PATENT DOCUMENTS 3,672,355 A 6/1972 Ogawa
3,935,869 A 2/1976 Reinsch
(Continued)

FOREIGN PATENT DOCUMENTS

GB 2492533 A 1/2013
RU 147082 U1 10/2014
(Continued)

*Primary Examiner* — Nvalerie L Woodward
*Assistant Examiner* — Paige Kathleen Bugg
(74) *Attorney, Agent, or Firm* — ArentFox Schiff LLP; Michael Fainberg

(57) ABSTRACT

The group of inventions relates to the field of medical technology, particularly to massage devices for personal use. The essence of the invention is a massage device capable of simultaneously stimulating two regions of the body, particularly through reciprocating sliding and reciprocating gyratory sliding along a span of movement comparable to the length of a vagina. This aim is achieved by a device comprising a first element, a second element, and a stimulating element comprising an electric means of acting upon the body of a user. The first element comprises a first surface section, and the second element is elongated and connected by its ends to the first element and to the stimulating element, which comprises a second surface section. The second element is bent and is capable of being elastically straightened and of moving the stimulating element from a first position.

16 Claims, 7 Drawing Sheets

(52) U.S. Cl.
CPC .. *A61N 1/36007* (2013.01); *A61H 2201/1664* (2013.01); *A61H 2201/1695* (2013.01); *A61H 2201/5023* (2013.01); *A61H 2201/5097* (2013.01)

(58) Field of Classification Search
CPC ............... A61H 23/02; A61H 23/0218; A61H 23/0254–0263; A61H 2023/0272–029; A61H 2201/0153; A61H 2201/0157; A61H 2201/12–123; A61H 2201/14; A61H 2205/085–087
See application file for complete search history.

(56) References Cited

U.S. PATENT DOCUMENTS

| | | | |
|---|---|---|---|
| 5,181,504 A | 1/1993 | Ono | |
| 5,690,603 A | 11/1997 | Kain | |
| 5,853,362 A * | 12/1998 | Jacobs | A61H 19/40 600/38 |
| 5,925,002 A | 7/1999 | Wollman | |
| D523,151 S | 6/2006 | Telford | |
| D523,152 S | 6/2006 | Telford | |
| D553,253 S | 10/2007 | Gayne | |
| D605,779 S | 12/2009 | Murison | |
| 7,658,707 B2 | 2/2010 | Topolev | |
| 7,717,867 B2 | 5/2010 | Nan | |
| 7,749,178 B2 | 7/2010 | Imboden | |
| D630,764 S | 1/2011 | Elliott | |
| D636,887 S | 4/2011 | Nan | |
| 7,931,605 B2 | 4/2011 | Murison | |
| D648,861 S | 11/2011 | Chong | |
| D652,946 S | 1/2012 | Chen | |
| D666,304 S | 8/2012 | Matsushita | |
| 8,419,611 B1 | 4/2013 | Hatami | |
| D694,897 S | 12/2013 | Small | |
| D699,366 S | 2/2014 | Marshall | |
| D700,347 S | 2/2014 | Sedic | |
| D700,350 S | 2/2014 | Tai | |
| D703,341 S | 4/2014 | Cohen | |
| D706,442 S | 6/2014 | Hahr | |
| 8,821,421 B2 | 9/2014 | Imboden | |
| D715,954 S | 10/2014 | Sedic | |
| D719,274 S | 12/2014 | Chen | |
| D727,524 S | 4/2015 | Qian | |
| D727,525 S | 4/2015 | Qian | |
| 9,028,395 B2 | 5/2015 | Jarzynski | |
| D731,667 S | 6/2015 | Elenga | |
| 9,050,240 B2 | 6/2015 | Howsam | |
| 9,114,056 B2 | 8/2015 | Imboden | |
| D738,520 S | 9/2015 | Lv | |
| 9,119,763 B1 | 9/2015 | Leary | |
| 9,119,765 B2 * | 9/2015 | Topolev | A61H 19/44 |
| 9,144,531 B2 | 9/2015 | Topolovac | |
| 9,192,254 B2 | 11/2015 | Gilbert | |
| 9,237,983 B2 | 1/2016 | Milton | |
| 9,254,238 B2 | 2/2016 | Lee | |
| 9,737,458 B1 * | 8/2017 | Olivares | A61H 21/00 |
| 2005/0273024 A1 * | 12/2005 | Nan | A61H 19/44 600/38 |
| 2008/0009775 A1 * | 1/2008 | Murison | A61H 23/0254 600/38 |
| 2008/0119767 A1 | 5/2008 | Berry | |
| 2009/0198158 A1 * | 8/2009 | Nan | A61H 23/0254 601/87 |
| 2009/0318755 A1 | 12/2009 | Adams | |
| 2011/0034763 A1 * | 2/2011 | Domnick | A61H 19/44 600/38 |
| 2012/0316390 A1 * | 12/2012 | Topolev | A61H 19/30 600/38 |
| 2013/0281892 A1 | 10/2013 | Godfrey | |
| 2014/0194794 A1 | 7/2014 | Sedic | |
| 2014/0228628 A1 * | 8/2014 | De Alva | A61H 19/50 600/38 |
| 2014/0309565 A1 * | 10/2014 | Allen | A61H 19/44 601/46 |
| 2014/0323929 A1 * | 10/2014 | Lurchenko | A61H 19/40 601/46 |
| 2014/0350333 A1 * | 11/2014 | Stout | A61H 19/44 600/38 |
| 2015/0231024 A1 * | 8/2015 | Sedic | A61H 19/50 600/38 |
| 2015/0359704 A1 | 12/2015 | Imboden | |
| 2016/0051438 A1 * | 2/2016 | Hahr | A61H 19/40 601/72 |
| 2016/0166466 A1 * | 6/2016 | Topolev | A61H 19/44 601/46 |
| 2016/0184178 A1 * | 6/2016 | Hahr | A61H 23/02 600/38 |
| 2016/0331629 A1 * | 11/2016 | Pearson | A61H 19/44 |
| 2017/0333282 A1 * | 11/2017 | Swartz | A61H 19/34 |

FOREIGN PATENT DOCUMENTS

| | | |
|---|---|---|
| WO | 2010120212 A1 | 10/2010 |
| WO | 2014/008606 A1 | 1/2014 |

* cited by examiner

MASSAGE DEVICE HAVING ELEMENT THAT STRAIGHTENS, METHOD FOR USE THEREOF, AND METHOD FOR MANUFACTURE THEREOF

CROSS-REFERENCE TO RELATED APPLICATIONS

This application is a National Stage entry of International Application No. PCT/RU2018/050086 filed on Jul. 27, 2018, which claims priority to Russian Patent Application No. 2017126944 filed on Jul. 27, 2017. the entire contents of which is hereby incorporated in its entirety by reference.

The invention relates to the field of medical equipment, to devices for stimulating reflex points, massage, and can be used for massage by rubbing, pressure, vibration of individual parts of the body, including genital organs. The massage device is used for personal massage, in purpose to satisfy sexual needs and can be used in domestic conditions, as well as in specialized institutions.

BACKGROUND

There is known from the prior art device for massage and sexual stimulation of the genitals "rabbit vibrator" comprising the main elongated member for vaginal stimulation and an additional elongated member with a front end designed for clitoral stimulation and connected with its rear end to the main member or its rear end. The free end of the additional element is directed to one side with the free end of the main member and slightly bent away from the main member. Wherein, the additional member is much shorter than the main member, that is its free end is shifted to the rear end of the main member, so that the longitudinal distance between their free ends is on average 100 mm. At this distance the main member of the "rabbit vibrator" is inserted into the vagina until the additional member abuts in the clitoris region, wherein the additional member has a small elastic mobility and it bends away from the main member as the main member is moved into the vagina at an average of 20 mm moving along in the clitoris region by about the same distance. Thus, such devices are able to perform reciprocating movements in the vagina (vaginal frictional stimulation), without stimulation of the clitoris or with short-term contact with the clitoris for a distance of up to 100 mm, and with simultaneous clitoral stimulation with constant contact with the clitoris up to 20 mm, despite the fact that the length of the main member, like a conventional vibrator without clitoral stimulation, is on average 150 mm. Therefore, the function performed by the devices can be attributed to clitoral stimulation with a feeling of fullness in the vagina without frictional stimulation. The disadvantage of such devices is the limitation of the distance of movement in the vagina of the main member with simultaneous clitoral stimulation by an additional member, as well as the displacement of the additional member from the area clitoral region with simultaneous stimulation.

There is known from the prior art device the vibrator Luxe Opus by company NSNOVELTIES, disclosed in the journal STOREROTICA Magazine, December 2015, p. 43. The said device comprises a convex clitoral stimulator elastically connected to a vaginal member, which is formed by two elongated members connected by their first ends to form a head part, as well as connected by their second ends to form a place for inserting of a user's finger between the elongated members. Such a design allows to use a clitoral stimulation with a slight angular movement of the vaginal member inside which the user's finger is placed and helps to perform deforming movements. The disadvantage of this device is the inability to produce significant vaginal stimulation over a distance of the length of the vagina with simultaneous clitoral stimulation.

There is known from the prior art international patent application PCT/RU2009/00055 publication WO/2010/044710 dated Apr. 22, 2010. The first embodiment of the device comprises an elongated member with a front end and a rear end, suitable for insertion into the vagina and a stimulating member suitable for stimulating the clitoral region, configured to move along the elongated member and spring-loaded from its rear end. This device provides constant contact of the stimulating member with the clitoral region during vaginal frictional stimulation, while the reciprocating movements of the elongated member are capable to a significant depth of the vagina, which is provided by the distance of movement of the moving stimulating member comparable to the length of the elongated member. The disadvantage of this device is that the movable member does not produce significant frictional movements for clitoris stimulation, as well as the complexity of the design, the presence of mechanically connected moving parts, which complicates the operation and maintenance of the device. Similarly, the second embodiment of the device comprises a vaginal member and a clitoral member, which is made with the ability of elastic displacement along the vaginal member and perform reciprocal movements transversally to the vaginal member. The disadvantage of this device is that the clitoral member performs slight reciprocating movements, about 20 mm, imparted to it by the wave-like driving grooves of the vaginal member, and is essentially limited to its diameter. In addition, due to the soft tissues of the entrance to the vagina, during the operation of the device there is no linear fixation of the movements of the vaginal member, and it can make wave-like longitudinal movements relative to the clitoral member, which, on the contrary, is fixed in the clitoris. Also the disadvantage of this device is the complexity of the construction, the presence of mechanically connected movable parts and an open internal structure, which complicates the operation and maintenance of the device.

There is known from the prior art application US2008/0154161 dated Jun. 26, 2008, disclosing a device with a rotating spherical member. The disadvantage of the device is the complexity of the design, the mechanical connection of the movable parts, the energy-dependent rotation drive, the absence of the return rotation, which assumes dependence on the constant supply of the lubricant.

The prior art patent U.S. Pat. No. 4,570,616 dated Feb. 18, 1986, disclosing a massager with two vibromotors, eccentric masses of which are offset from each other by phase angles, as well as U.S. Pat. No. 4,891,954 dated Jun. 27, 1989, disclosing vibromassage glasses comprising an electric motor with a shaft extending on two sides, on which two eccentric masses are mounted without shifting the phase angles and, alternatively, with shift thereof. The disadvantage of the device is the lack of elastic fixing of the motor with a certain free displacement i.e. large amplitude of mechanical vibrations for massage effects.

The prior art patent design EM002078162-0001 publication date Aug. 1, 2012 (CA149467 registration date Nov. 14, 2013, U.S. D694,897 registration date Mar. 12, 2013), which is a round-shaped vibrator with a longitudinal round recess, framed on both sides by arcuate wing-shaped elements bent into inward, with rounded ends smoothly passing into the recess. The penis is placed in the said recess, which is gripped by the wing-shaped members and pressed against the zone of location of the vibrating member. The disadvantage of this device is the impossibility of simulating coitus, that is, performing reciprocating movements along the penis, while maintaining the vibration zone on the glans penis, which is the most sensitive erogenous zone responsible for the onset of orgasm.

The prior art patent design EM001171722-0001 publication date May 11, 2009 which is an elongated vibrator at one end with a blind hole with an elastic sleeve designed to insert a penis into it, and a transverse cylindrical vibration block at the second end. The disadvantage of this device is the limited movement of the penis in the hole, while maintaining the vibration zone on the head of the penis, since the vibration block is rigidly connected to the body of the elastic cuff, as well as the insignificant distance of the possible movement of the penis inside the cuff, which is much less than the average length of the erect penis. Male masturbators are also widely known, which are elastic sleeves with a channel simulating a vagina, including one located inside, in depth, or several, along the channel with vibrators. The disadvantage of such devices is the displacement of the vibration zones as the penis is inserted into the masturbator relative to the head of the penis, which means intermittent vibratory action on the erogenous zone.

The prior art device is disclosed in the international application for invention PCT/RU2006/000121 publication WO/2006/110066 dated Oct. 19, 2006. The device comprises a first elongate member having a first end and a second end, and a second elongate member having a first end and a second end connected to each other with their first ends, wherein the members connector is adapted to be inserted into the vagina. Wherein the second elongated member is flexible with the ability to stimulate the clitoris and provides constant contact with the clitoris during vaginal frictional stimulation with a significant distance of movement, comparable with the length of the vagina. The disadvantage of this device is that its operation is carried out by holding the second end of the first member and imparting a translational movement to the inside of the vagina by one hand and by the second hand while holding the second end of the second member in translation so that it moves inside the vagina following the first member and stimulates clitoris by rubbing inward or from top to bottom. In reverse movement of the first member outward from the vagina, the second member must be pulled following the first member so as to stimulate the clitoris outward or upward, which is difficult to synchronize in the rhythmic reciprocating movement. The presence of a tension device connected to the second elongated member makes it possible to operate the device with one hand, but at the same time complicates the design of the device and creates the problem of fixing the tension device. Moreover linear stimulation, in which a flexible, essentially band-shaped member envelopes around the pubic bone, in addition to the clitoris area, also stimulates adjacent genital areas, which can distract and interfere with concentrating on sensations of clitoris stimulation, as well as the directions of stimulation by the clitoris and the vagina match. The lack of vibration action to the clitoris is another disadvantage of the analogue.

In the prior art can include the following patent documents defining the overall level thereof: US2016/0051438; US2015/0359704; US2015/0231024; US2014/0194794; US2009/0318755; US2008/0119767; RU147082; RU2509548; RU2289385; RU2009115726; U.S. Pat. Nos. 9,254,238; 9,237,983; 9,192,254; 9,144,531; 9,119,765; 9,119,763; 9,114,056; 9,050,240; 9,028,395; 8,821,421; 8,419,611; 7,931,605; 7,749,178; 7,717,867; 7,658,707; 5,690,603; 5,853,362; GB2492533; U.S. Pat. Nos. 5,925,002; 5,181,504; 3,935,869; 3,672,355; WO/2010/00682; WO/2014/008606; US2013/0281892, U.S. D523,151; U.S. D523,152; U.S. D553,253; U.S. D605,779; U.S. D630,764; U.S. D636,887; U.S. D648,861; U.S. D652,946; U.S. D699,366; DM/087783; U.S. D666,304; U.S. D700,347; U.S. D700,350; U.S. D703,341; U.S. D706,442; DM/084346; U.S. D715,954; U.S. D719,274; U.S. D727,524; U.S. D727,525; U.S. D731,667; U.S. D738,520; EM001268429-0001; EM002774851-0001; CN201630027618.7; CN201630027901.X.

The closest analogue and prototype of the invention is the NOVA vibrator by We-Vibe, disclosed in STOREROTICA Magazine, December 2015, p. 42, And in patent application PCT/CA201605800, publication WO/2017/004721 of Jan. 12, 2017, which comprises a vaginal stimulating member with a vibrator and a clitoral stimulating member with a vibrator, which is configured of longitudinal angular elastic movement relative to its arc-shaped base. Wherein the clitoral stimulation is provided not by the end of the clitoral member, but by its outer longitudinal surface. According to the drawings, the end of the vaginal member protrudes longitudinally relative to the stimulating surface of the clitoral member by 52 mm, while the distance from the end of the vaginal member to the stimulating surface with a maximum elastic angular displacement of the clitoral member to the arc-shaped base is 80 mm. Therefore, this device is capable of simultaneously stimulating the clitoris and vagina with reciprocating movements over a distance of 28 mm. In this case, an angular rocking movement of about 60 degrees relative to the clitoral member is possible, however, such movements are limited and provide a useful vaginal movement within 40 mm. Also due to the angular mobility of the clitoral member relative to its arc-shaped base, the clitoral member can produce minor reciprocating movements, or rubbing, along the clitoris within 15 mm. But if the clitoris head has a natural mobility of 15 mm, then friction, that is frictional stimulation, does not occur between the clitoris and the clitoral member, or it is insignificant. The length of movement of the clitoral member from the open position to the compressed position is limited by the flexibility of the connecting portion, which is fixed to the proximal end of the vaginal portion. The disadvantage of this device is the limited distance of movement of the vaginal member into the vagina with simultaneous clitoral stimulation, the absence of a rectilinear massage effect by rubbing on the vagina, as well as insignificant frictional stimulation of the clitoris.

Unless defined otherwise, all technical and scientific terms used herein have a meaning similar to that commonly understood by those skilled in the art to which this invention pertains. The terms "massage affect", "grinding", "pressure", "vibration", "stimulation", "friction", "rubbing" are generally used in relation to massage and sexual effects on the soft tissues of the human genitalia. The term "orbital rotation" is used to refer the massage affect of the friction of each point on the surface along a closed circular path. The term "rotation" is used to describe a movement of members relative to each other along an axis for a full revolution or a certain angle or along a circular path.

The premise of the invention is the observation that the most sensitive erogenous zone of the female genitals is located in the region of the clitoris, and the most sensitive zones of internal genitals are located at the entrance to vagina, and may also be located in the middle part, known as "G-spot", and on vaginal vault in the area of the cervix.

This means that simultaneous stimulation of these zones is most effective for orgasm and contact of the clitoral member with the clitoris should occur immediately upon initial insertion of the vaginal member, and continue until the vaginal member is fully inserted into the vagina. In addition, the clitoris, responsible for achieving orgasm, is located at the distance from the entrance to the vagina and can be moved away from it when excited. There are at least two types of its stimulation: direct stimulation of the clitoral region and its head by rubbing with the hand, tongue, penis, etc., or indirect stimulation of the clitoris through the so-called "legs" located on both sides of the vaginal opening, along which sexual impulses are transmitted during frictional stimulation of the vagina by the penis. According to research by experts, in most cases, achieving an orgasm is possible using the first method. However, in some women, the clitoris is located close to the vaginal entrance, so that there is direct stimulation of the clitoris by the penis friction with simultaneous movement of the penis in the vagina, and they are able to experience stronger orgasmic sensations. Thus, the most effective sexual stimulation is reciprocating motion in the vagina of the elongated member and synchronous reciprocating motion of the stimulating member along the clitoris, in particular, on its head. It is known to those skilled in the art that the excited penis of a men has an average length of 15 cm, the length of the its head is 3-5 cm and it is permanently located in the vagina during the frictional stage of the coitus, so that the penis is not drawn completely outwards. Consequently, the working stroke of the penis by 100-120 mm can be considered a useful movement of the penis into the vagina. This means that for effective stimulation of the clitoris, the stimulating surface of the clitoral member should have the length commensurate with the length of the vaginal member or the useful movement (stroke) of the vaginal member into the vagina. The use of a rectilinear member to stimulate the clitoris requires the presence of a free space to move it, and in the case of vaginal stimulation, this space occupies the vaginal member. Unlike vaginal stimulation, at which full contact between the vagina and vaginal member is necessary, the clitoris area has limited site, and the head of the clitoris, it can be said, has the point site and the spot of contact with the stimulating member has insignificant dimensions. Thus, the useful surface for the purpose of reducing the physical dimensions can be arranged in a curve, for example in an arc. Thus, when using a rounded stimulating member with a diameter of 20-30 mm, the required length of the stimulating surface of 100 mm is achieved by rotating the said member at 290-190 degrees. Wherein the increase in diameter reduces the necessary angle of rotation of the stimulating member. In this case, the curvilinear, substantially circular surface provides stimulation of a similar rectilinear surface, which has a compact size, which makes it possible to place the clitoral member in close proximity to the vaginal member so that their movements do not interfere with each other. Wherein it is necessary to associate reciprocating movement of vaginal member and reciprocating rotational movement of clitoral member, so that the user would receive synchronous sexual impulses, as well as be able to control them predictably. The reciprocating rotational movement of the clitoral member is felt as a natural stimulation by the penis, and has the advantage that the convex surface provides more stimulation of the clitoris head than the surrounding tissues, due that the portion of the contacting surface of the clitoral member is protrudes relative to the surrounding portions. In addition, during the reverse-rotational movement, the lubricant is constantly in the contact zone, and in the case of unidirectional rotational movement, it is gradually removed from the contact zone, and in addition, the different directional synchronous action of the friction of the vagina and clitoris gives additional exciting sensations. To implement such stimulation, it is necessary to elastically connect the vaginal member and the clitoral member with each other with an elongated curved connecting member connected to the distal end of the vaginal member and configured to unbend to a developed angle along the vaginal member and have high elastic deformation properties and the ability to be inserted into the vagina together with the vaginal member upon approaching which it forms, essentially, another vaginal member suitable for insertion into in the vagina. The expansion of functionality gives the presence of vibrational affects on the clitoris, which greatly enhances the massage and sexually stimulating effect. Wherein vibration motors with an eccentric mass are mainly used, in the process of rotation of which there are centrifugal, centripetal, inertial, and other forces that deflect the clitoral vibrator from its axis, and if it is elastically suspended relative to the handle of the massage device, then its displacement can complicate operation. Moreover, the possibility of elastic displacement of the clitoral vibrator relative to the handle of the device gives the advantage of the ability to use harmonic oscillations with a large amplitude and in different directions, which can be implemented in a device whose clitoral vibrator is mounted on an elastic and elongated member, giving a certain freedom of movement relative to the handle of the device, for example longitudinally to the vaginal member. In addition to rotational reciprocating movements, as an alternative for women with a sensitive clitoris, stimulation is possible without displacing the stimulating member along the clitoris, but only due to elastic pressure, i.e. pressure on sensitive zones and vibration affect. In this case, the clitoral member should be movably connected to the elastic connecting member and have an angular rotation along the direction of movement of the vaginal member, wherein the axis of rotation should be located approximately in the middle of the clitoral member at a distance of 20-30 mm from the vaginal member. The movable connection can be made detachable or one-piece, articulated, axial, or due to elastic deformation of the connecting portion, and should provide an electrical connection between the clitoral member in which the vibrator is located and the vaginal member in which a power supply means and a control means of vibrator of the clitoral member are located, or the clitoral member may comprise an autonomous vibration unit. An additional advantage of using a clitoral stimulator without displacement, or static, is that possible increase the area of stimulation, for example, made it with a flattened surface in the shape of the clitoral region and thereby provide contact with the clitoral region even if it is located at the very entrance to the vagina, unlike a rounded member, the surface curvature of which does not provide such contact, since the preferred radius of the surface arc is 20-30 mm, and should be placed at such a distance from the entrance to the vagina the clitoral region for its contact with the rounded stimulating member, which can be corrected by the tension by the hand of the tissues of the clitoris region. Another advantage of the static clitoral member is that it can be extended and thereby make the stimulating surface forward beyond the distal end of the vaginal member and allow the vaginal member to be completely pulled out of the vagina without losing contact of the clitoral member with the clitoral region, which diversifies the user's sexual sensations.

For a man, simultaneous stimulation of two erogenous zones is necessary to reach orgasm in most cases. Stimulation by friction or vibration of only the head of the penis without affecting the shaft of the penis may occasionally cause orgasm, but for completeness of sensations and complete sexual discharge, it is not sufficient, since there is no imitation of sexual intercourse, namely its copulatory stage with frictional stimulation of the penis by reciprocating its in the vagina. It is known to those skilled in the art that the excited penis of a men has an average length of 15 cm, the length of the its head is 3-5 cm and is permanently located in the vagina during the frictional stage of the coitus, so that the penis is not drawn completely outwards. Consequently, the useful stroke of the penis in the vagina can be considered as the working stroke of the penis by 10-12 cm. This means that for effective stimulation of the penis it is necessary to continuously act of its head and its base with two stimulating members, resiliently connected to each other, one of which is continuously pressed to penis head and the second one moves along its shaft from base to head by 10-12 cm. Making one stimulating member with the ability of reciprocating rotational movement on the head of the penis in the process of reciprocating movement of the second stimulating member through along the shaft of the penis enhances stimulating action and accelerates the achievement of an orgasm.

The object and technical result of the invention is a creation of a device for simultaneous affecting to two parts of the body, providing an increase in the area of affecting to one of them by a distance approximately equal to the length of the vagina, eliminating the disadvantages of analogues, simplifying the construction, increase of reliability and expanding the technical functionality and arsenal of technical means for massage of the genital organs and obtaining the in first time the claimed device. Additional objects and technical results are: an increase in the area of the clitoris area available for continuous massage by pressing the flattened surface against the clitoral region, while simultaneously allowing the vagina with massage action by translational movement over the whole length thereof; allowing the flattened surface to contact when the connection of the first ends of the first member and the second member from the vagina is completely pulled out; allowing the stimulating member with the ability of applying various vibrational effects in the form of different directions of oscillations, as well as maintaining these directions in the process of moving the stimulating member and preventing its lateral displacement during oscillation generation; allowing the stimulating member with the ability to prevent lateral shift relative to the bending plane of the second member; providing the possibility of continuous massage effects by rotating a rounded surface along the clitoris with simultaneous and synchronous provision of the vagina with massage effects by translational movement over its entire length; adding the ability of the stimulating member the ability of rotational movement along the clitoral region in the bending plane of the second member in the direction from the entrance to the vagina during the movement of the stimulating member along the first member by a distance of the length of the vagina from the first position to the second position due to the pushing force of the clitoris on the stimulating member with the joint insertion of the first member and the second member into the vagina, and towards the entrance to the vagina during the movement of the stimulating member from the second position to the first position due to the pushing force of the second member on the stimulating member while pulling the first member and the second member out of the vagina, the length of the arc of rotational movement essentially coinciding with the length of the vagina; ability of affecting with the first body portion (the vagina or trunk of the penis) and the second body portion (the clitoris or the head of the penis) by members elastically connected to each other, the first of which configured of its translational movement along the first body portion, and the second is configured pressing it against the second body portion during the translational movement, at a distance approximately equal to the length of the vagina or penis and simulating the friction stage of coition in the vagina; increasing the efficiency of the affection of the second member on the second body portion by making the device with the ability of rotational movement of the second member along the second body portion as the first member is moved in translation along the first body portion; allowing a clitoral region with a continuous massage action, including vibration, in the process of allowing a vaginal massage action with a reciprocating movement along the entire length of the vagina, a device simulating the frictional stage of coitus and performing simultaneous stimulation of the clitoris; allowing the clitoral region with a continuous massage action, including vibration, rotational back and forth movement, including an obtuse angle, with a surface approximately equal to the length of the vagina, in the process of allowing the vagina with massage action back and forth movement along the entire length of the vagina, by a device that simulates friction coitus stage and performing simultaneous frictional stimulation of the clitoris.

This is obtained by creating a device for massage of genital organs, comprising means for controlling an electric means of affecting the human body, a first member, a second member and a stimulating member comprising said affecting means. The first member comprising a first surface portion is configured to affect a first human body portion, the second member is made elongated and connected by its first end to the first member, and by its second end connected to the stimulating member, which comprises a second surface portion is configured to affect a second human body portion. The first surface portion is configured to a translational slide along the first human body portion, and the second surface portion is configured to press against the second human body portion during the said translational sliding. The second member is made with a curvilinear bend and is configured to elastically unbend and thereby move the stimulating member from the first position, in which the second surface portion is closer to the first surface portion, to the second position at which the second surface portion is distant from the first surface portion. The second member is configured with the said ability to elastically unbend as the said translational sliding and thereby move the stimulating member essentially parallel to the opposite direction of the said translational sliding and to press it by the second surface portion to the second human body portion in the process of the said translational sliding. The second member is made of an elastically deformable material and contains flexible electrical conductors that electrically connect the said control means with the said affecting means, and a flexible surface portion is configured jointly with the first surface portion of the said translational sliding and transform from a curvilinear shape into an essentially rectilinear shape as the said translational sliding.

Additional features are: the said affecting means comprises at least one stimulation means, for example, a vibration means, which is configured to impart a rotational movement to a vibration-generating mass, for which, for example, it contains an electric motor with an eccentric mass mounted on its output shaft, or with an ability to impart the vibration-generating mass reciprocating movement, for which, for example, contains a coil member with a movable ferromagnetic core, or motion means, or electric stimulation means, or means of heating a surface, or a combination thereof, the control means contains at least one electric current source, for example, a rechargeable battery, including a lithium-ion battery is adapted of charging by a contact, including by contacts made from electrically conductive elastically deformable material, or in a non-contact method, and at least one control means of the stimulation means, including with variety settings, with elastically pressing buttons and light indication, for example LED, including with an ability to remotely control it, for example via a smartphone using radio connection by Bluetooth; the stimulating member comprising at least one vibration means is configured to perform orbital vibrations in the plane of the second human body portion, for which, for example, it contains an electric motor, a shaft axis of which essentially coincides with the direction of the said translational sliding, and the plane of rotation of the eccentric mass is essentially transverse to the plane of bending of the second member, or the stimulating member contains at least one vibration means, made with the ability of generating linear oscillations, for example, a coil member with a moving ferromagnetic core or a directional action vibrator with shafts synchronously rotating in opposite directions, exciting a linear harmonic disturbing force directed to the second human body portion essentially parallel to the direction of the said translational sliding, or across it along plane of bending of the second member, or across it across plane of bending of the second member, or the stimulating member contains at least one vibration means, made with the ability of generating angular oscillations, for which, for example, it contains an electric motor with an output shaft on two sides on which two eccentric masses are mounted, the phase angles of which are rotated relative to each other along the shaft axis by 180 degrees, with an oscillation plane essentially, the transverse plane of the bend of the second member or coincides with it, or the stimulating member contains at least one vibration means, made with ability to maintain the direction of oscillation in process the movement of the stimulating member from the first position to the second position, for which, for example, it contains an electric motor whose shaft axis essentially coincides with the bending axis of the second member, or contains a coil member with a movable ferromagnetic core whose direction of movement is essentially longitudinal to the bending axis of the second member, or the stimulating member comprises at least one vibrational means made with ability to prevent lateral displacement relative to the bending plane of the second member, stimulating member in the process of generating vibration, for which, for example, it contains an electric motor mounted transversely to the bending plane of the second member, for example, with an eccentric mass mounted on it, the rotation plane of which essentially coincides with the bending plane of the second member, and the shaft is fixed symmetrically said eccentric mass, or with an output shaft on two sides on which two eccentric masses are mounted without phase shift between them, whose rotation planes are essentially coincide with the bending plane of the second member and spaced symmetrically to it, or contains a coil member with a movable ferromagnetic core mounted transverse to the bending plane of the second member and generating vibrations perpendicular to the bending plane of the second member; the second member is configured to prevent lateral, relative to the bending plane of the second member, displacement of the stimulating member, for which it is made with a force of elastic deformation in the transverse direction exceeding than the force of elastic deformation in the longitudinal direction, for example, its transverse the cross section is elongated across the bending plane, and/or it comprises an elastic strip, for example of spring metal, mounted its wide side transverse to the bending plane, which provides longitudinal deformation and prevents transverse deformation, and has, for example the ratio of width to thickness in the approximate range of from 10:1 to 100:1, preferably 50:1; the stimulating member is elastically suspended relative to the first member and is capable of lateral elastic deflection relative to the first member, which provides the second member, and contains a vibration means, for example with an eccentric mass, whose inertial forces acting on the stimulating member distributed uniformly relative to the axis of deflection of the stimulating member and which essentially coincides with the plane of bending of the second member, or with two or more eccentrics masses, internal forces of which acting on the stimulating member is uniformly distributed relative to the axis of deflection or compensate each other; the device is made showerproof or waterproof with a surface of silicone rubber, for example, made monolithically of silicone rubber or covered with silicone rubber, or a combination thereof, for example, the first member, the connection of the first member and the second member and the stimulating member is covered with silicone rubber, and the second member is made monolithically of silicone rubber, and the surface is made, for example, monolithically closed and smoothed, or with a developed relief structure, for example, an imitating penis or vagina, comprising protrusions, for example, for enhanced stimulation of the «G-spot» and/or indentations, matte, glossy, or a combination thereof; the device comprises an inner frame and/or an inner body made of plastic and/or metal, which comprises and/or connects, including mechanically, for example, movably, the affecting means and/or the control means, and the second end of the first member is configured to be held by hand and/or to be connected to a surface or to a means of movement, or connected to means configured to be held by hand and/or to be connected to a surface or with a means of movement; the first surface portion is configured to massaging affect, including friction and vibration, on the human cavity, and the second surface portion is configured to massaging affect, including friction and vibration, on an adjacent the portion of the human body, in the first case, the first human body portion is the vagina, in particular its front wall, and the second human body portion is the area of the clitoris, in particular its head, and in the second case, the first human body portion is the anus, and the second human body portion is the crotch, and the flexible surface portion is configured to unbend as the said translation sliding along the first human body portion and thereby form an essentially inverse shape of the first human body portion, for example, a semi-cylinder, for which the second member is made of an elastomer, for example, silicone rubber; the first member is made elongated, with the first end connected to the first end of the second member in the direction of the essentially first member, so that the bend of the second member is directed away from the first member, and configured to jointly with the first end of the second member insert into the vagina and comprising a second electric means to affect on the human body, and the second end is adapted of holding by hand, and contains the electric current source and the control means and comprises a rectilinear, or made with a slight arcuate bend in the plane of the bend of the second member, with the rigidity necessary for insertion into the vagina, portion in the direction of which the second member is connected and along which the second member is configured to unbend and thereby form essentially of the erect penis, and move the stimulating member essentially along this rigid portion from the first position, in which the stimulating member is brought closer to the first end of the first member in the second position in which the stimulating member is close to the second end of the first member, at a distance approximately equal to the length of the vagina; the first member is made elongated, with the first end connected to the first end of the second member in the direction of the essentially first member, so that the bend of the second member is directed away from the first member, and configured to jointly with the first end of the second member insert into the vagina and comprising a second electric means to affect on the human body, and the second end is adapted of holding by hand, and contains the electric current source and the control means and comprises a rectilinear, or made with a slight arcuate bend in the plane of the bend of the second member, with the rigidity necessary for insertion into the vagina, portion in the direction of which the second member is connected and along which the second member is configured to unbend and thereby form essentially of the erect penis, and move the stimulating member essentially along this rigid portion from the first position, in which the stimulating member is brought closer to the first end of the first member in the second position in which the stimulating member is close to the second end of the first member, at a distance approximately equal to the length of the vagina; the first surface portion is configured to massaging affect, in particular friction and vibration, on the shaft of the penis, in particular on its lower surface, and the second surface portion is configured to massaging affect, including friction and vibration, on the head of the penis, the flexible surface portion configured to unbend as said translation sliding along the first human body portion and thus to take the shape an essentially inverse form of the first human body portion, such as a gutter, for which the second member is made of an elastomer, such as silicone rubber; the stimulating member is movably connected to the second end of the second member, including mechanically and releasably, providing electrical connection of said affecting means with said conductors, for example, with axial rotation in the plane of bending of the second member, the second member is made with essentially bending in a spiral, the second end of the second member is configured to move from the first position to the second position essentially parallel to the opposite direction the said translational sliding, wherein the second surface portion is configured to prevent sliding along the second human body portion, for example, with a flattened surface that can be extended forward from the first surface portion and is configured to provide massage by pressure and by the said affecting means of the second human body portion, both in the process of the said translational sliding and without contact of the first surface portion with the first human body portion; the stimulating member is elastically connected to the second end of the second member and is made rounded in convex in the plane of the bend of the second member, including an arc-shaped, for example, C-shaped, second surface portion is configured to provide massage affects by pressure, rubbing and the said affecting means on the second human body portion and with the ability of rotational sliding on the second human body portion in the plane of the bend of the second member in the direction from the first human body portion in the process of transformation from the said first position to the said second position due to the pushing force of the second body part on the stimulating member in the opposite direction of the said translational sliding when the second surface part is pressed into the second body part, and towards the first body part in the process of transformation from said second position to said first position due to the pushing force of the second member on the stimulating member in the direction of said translational sliding during restoration of the second member of its original shape, wherein the length of the arc of rotational sliding being approximately equal to the length of the vagina, the first member is configured to hold by a hand and to impart reciprocating sliding to it with the first surface portion over the first human body portion, and the second member is configured to impart to the stimulating member of the reciprocating sliding of the second surface portion along the second human body portion, and the second member is made of substantially the same surface as the second portion, including the arc-shaped, for example, C-shaped bend so that their centers of arcs are substantially coincident, and partially envelopes a second surface portion; the first member and the second member have a substantially semicircular cross-section, with fillets between the arc and the chord, of approximately the same size, height in the approximate range of 5 to 45 mm, preferably 16 mm and width in the approximate range of 10 to 90 mm, preferably 30 mm, and/or when approaching, their cross sections form essentially a circle, the first member, the second member and the stimulating member are integrally formed and/or smoothly connected to each other, connections of the first member and the second member is made essentially end-face and forms a distal end of the device, made round and contains vibration means, the stimulating member is made in the form of a body of revolution, for example, spherical shape with a stimulating surface formed in an arc in an approximate range of 90 degrees up to 330 degrees, preferably 240 degrees, essentially circumferentially, with a radius in the approximate range of 15 mm to 45 mm, preferably 25 mm, in the bending plane of the second member, with the arc facing towards the connection of the first member and the second member, the second member is made with a bend along an arc in the approximate range of 90 degrees. up to 270 degrees, preferably 125 degrees round a circle with an outer radius in the approximate range of 25 mm to 60 mm, preferably 43 mm, and has a substantially single center with said surface.

The essential of the invention is an elongated curved elastic member comprising a portion of a surface which, as it unfolds, becomes able to act on a portion of the body.

The said essential features can be implemented in the device for massage of the genitals (hereinafter-massager) in which the first member is elongated with a rounded portion suitable for insertion into the vagina, or with a rounded longitudinal opening or recess for placing penis into it. The elastically of the first member is provided by a material of manufacture, for example, a silicone rubber having a hardness of 20-80 A Shore, preferably 40A Shore, or by the presence of a resilient member, such as a core made of metal or plastic. The first member is designed with a curvilinear bend, preferably arc-shape, and is connected to the second member. The second member has a movable connection including resilient with the first member, which provides its pressing against the clitoris or the head of the penis during the movement of the first member into the vagina or along the penis. The device can be designed as a universal means for use by women or men. In the first case, the second member is placed on the clitoral region and the first member is inserted into the vagina by its second end, it is given a rotational movement, by means of which its second end pushes into the vagina, the first member is unbent, and the second member is given rotation. In the second case, the second member is placed on the penis head and the first member moves along the penis to its base, wherein the first and second members located on opposite sides of the penis. When the second end of the first member advances towards to the penis base, its deformation occurs, it unbends and imparts rotation to the first member along the penis head. For convenience of use, the first surface portion and the second surface portion may be made with a flattening or recess for placing the penis. Also, the second member may have an indirect interaction on the penis head, for example, by providing a second member with a vibrator, and the first member is made in the form of flexible sleeve with arc-shaped bend, the first end of which is adapted for insertion of the penis and the second end is resiliently connected to a vibratory device, for example, a round shape. In this case, the sleeve envelopes the vibrator, which is pressed resiliently to it. This technical solution allows continuous stimulation of the penis and its head by friction, as well as allows a constant location of the vibration device on the head of the penis, which is pressed by the elasticity of the first member through its wall and transmits mechanical vibrations to the head of the penis, the constant location of the vibrator in the region of the head is provided by the elastic deformation of the sleeve, which expands upon insertion of the penis and the head pushes the vibrator in the direction of insertion.

Said essential features can be realized in a massager in which a first member is made elongated with first end and second end, has a length from 120 mm to 250 mm, preferably 180 mm, made straight or with a slight curvilinearity, for example, with a curved arc with a radius of 200 mm to 600 mm, preferably 400 mm, which has the property of rigidity or resilient sufficient for insertion into the vagina. The second member of the device is made with a curvilinear bend away from the first member, for example, along an arc with a radius from 25 mm to 60 mm, preferably 43 mm by an angle from 90 degrees to 270 degrees, preferably 125 degrees with the property of resilient necessary and sufficient for resilient bending along the additional member and restoring its original shape, and also with the necessary and sufficient pressing force of the second member to the clitoris area. The cross-section of each said members is essentially part of circumference with a segment from 150 degrees to 270 degrees, preferably 180 degrees, with rounded corners, a height of from 5 mm to 45 mm, preferably 16 mm, with a width of from 10 mm to 90 mm, preferably 30 mm. Wherein It is preferred that the cross-section of the first member and second members form an essentially a whole circle, since parts of the circumference form the outer surfaces of said members and are thus able to mimic the shape of the penis. In addition, increasing the thickness of the second member allows to manufacture it from a material with a lower rigidity of about 40A Shore, without an inner resilient core, which is preferable in the monolithic construction of the massaging part of the device. And also, approximately half the thickness of the second member from the total thickness with the first member, allows to optimal ratio between longitudinal displacement of stimulating member and its lateral displacement. The connection of the first member with the second member is implemented by their first ends, and is essentially an end connection. Wherein, the longitudinal axis of the first member lies approximately in the plane of bending of the second member. Said connection forms a convex rounded shape, which is essentially the distal end of the massager (front end, head part). It can be made of a body of rotation, for example, in the form of an ellipsoid with the first diameter from 20 mm to 60 mm, preferably 35 mm, and a second diameter from 30 mm to 90 mm, preferably 60 mm, and comprises at least one electro-mechanical means for creating mechanical vibrations (hereinafter—vibrator) and the device comprises power supply source and control means. Additionally, the said connection can be made with a protrusion to stimulate the "G"-spot. The second member is connected to the stimulating member, which performs the function of a clitoral stimulator and can be implemented as essentially with a flattened, for example, in the shape of the clitoris region with a slight concavity, and a convex, essentially rounded, surface. The connection of the stimulating member and the second end of the second member can be made with a movable connection, including electrically conductive, providing angular or axial movement, including elastic, in order to ensure that it is pressed against the outer area of the clitoris during insertion of the connection of the ends of the elongated members into the vagina and provide static contact without displacement, not including vibrational, stimulating surface in the clitoral region. In some embodiments, the stimulation member may be made as an extension of the second member, in which case it is determined from the starting point, which is suitable for contact with the clitoral region in the initial insertion, performing its function. Wherein the starting point of the surface, suitable for stimulation of the clitoris, is located near the junction of elongated members, with a longitudinal displacement, both towards the second end of the first member, and in the opposite direction, which allows the stimulating surface to be moved forward, so that, before, or during the initial insertion of the junction of the first ends, the vagina contacts the specified point with the clitoris. If the perpendicular from said point to the longitudinal axis of the joint of the elongated members is lowered, which approximately coincides with the axis of the vagina or the axis of insertion, the distance from the tip of the distal end of the massager to the point of intersection with the normal will be from −30 mm to 90 mm, preferably 35 mm, and the distance from this point to the intersection of the perpendicular with the surface of the connection of the elongated members will be from 20 mm to 50 mm, preferably 35 mm, which is actually the distance between the clitoris and the vaginal entrance. From the said initial point, in plane of bending of the first member, the stimulating surface is formed along circle with radius from 15 mm to 45 mm, preferably 25 mm, along an arc of 90 degrees up to 330 degrees, preferably 240 degrees. In this case, the center of the arc faces in the direction close to the substantially perpendicular to the first member, or deviates from perpendicular in longitudinal plane by not more than 45 degrees. The stimulating member may be smoothly connected to the second end of the second member so as to be integral therewith, so that the second end of the second member performs the function of a stimulating member. The radius of the arc of the stimulating member is less than the radius of the arc of the second member, and they may form a spiral shape, for example by means of connection to each other by another arc having average arithmetic radius of arc of the stimulating member and radius of arc of the second member. In addition, the overall shape of said members may be an arbitrary spiral, or Archimedes spiral, or Ferma spiral, or a combination thereof, that most preferable with combination with the movably connection of stimulating member. The shape of the stimulating member can be made of a body of revolution, for example, in the form of a ball, wherein the second member envelopes the stimulating member, including the non-convex angle, also with flattened, with protecting sliding protrusions of stimulating member. Since the first member is rigid and the second member is elastic, their properties can be provided by monolithic manufacture of elongated members from elastically deformable material, for example, a silicone rubber having a Shore A hardness of from 5 to 80, preferably, 40, wherein the first member can comprise a rigid core or an inner body or a frame, and the second member can also have a core made of a resilient material or not have it. The described design allows the stimulating member to be displaced by a distance of up to 200 mm, preferably 150 mm, and perform by the massager reciprocates in the vagina by approximately the same distance. This is achieved due to the arc-shaped bend of the second member, which elastically unbends along the first member. Essentially, the arc of the second member rolls out along the straight linear member and acquires the linearity of the first member, thereby imparting to both of the members a shape imitating the erect penis. In this case, the stimulating member performs a turn in the plane of bending of the second member, wherein the axis of rotation remains approximately at one distance from the axis of insertion, as a result of which the stimulating member remains in the zone of contact with the clitoral region during the whole length of insertion of the device. This is achieved by the fact that the insertion of the distal end of the massager is performed by inserting the connection of the elongated members and moving it deeper into the vagina by means of the first member held by the second end, which can have a convenient handle, for example a spherical shape. Besides, the second end of the first member can be arranged with the ability of installation on a smooth surface, for which it is equipped, for example, with a suction cup, or with the ability of being connected to the human body, for which it is provided, for example, with a shape providing a connection with a belt (harness) or with a shape suitable for insertion into the vagina of another user, or with the ability of being connected to a mechanical device (sex machine), for which is provided, for example, with a profile lock-adapter (vacuum lock). At the beginning of insertion, or the first position the stimulating member abuts against its starting point of surface in the clitoral region, and by means of the connection to the second member, pushes the second member, which under the action of force unbends along the first member. The length of the arc of the second member is reduced and the second member pulls the stimulating member behind it, which results in its rotation relative to the axis of the arc of the surface, commensurate with the length of the arc, and also presses it to itself, and in the case of an axial connection, it rotates relative to the static stimulating element. Essentially, at the stimulating member shifts the attachment point along the insertion axis, and thus the point of contact of the stimulating surface with the clitoris has approximately the same distance from the axis of insertion throughout the entire displacement distance of the stimulating member. This gives an advantage over a fixed point of attachment that is only possible with shift to the proximal end, which implies an elongation of the stimulating member, an increase in the radius of the arc and its distance form the axis of insertion at the deformation, along which for the arc shifts the stimulating member. When the distance of insertion in the vagina is reached, or the second position, the first member is given an inverse linear movement, and under the action of the elastic forces the second member returns to the initial position and constant presses the stimulating member against the clitoral region. Since the frictional stage does not assume complete removal of the massager from the vagina, the stimulating member does not lose contact with the clitoral region, but in the case of protruding of the stimulating surface forward for the connection of the first ends, it is able to completely remove it for a variety of sexual sensations. Further, the cycle of reciprocating movement of the massager is repeated, and thus the stimulating member is given a reciprocating-rotational movement, or axial connection compensate this turn.

Additionally, the device may comprise all of the components known in the prior art, inherent in a modern massage device with a similar purpose. In order to enhance the massage and stimulating effect, the massager can contain at least one vibrator, which is arranged to impart a rotational movement to the vibration-generating mass, for which, for example, comprises an electric motor with an eccentric mass mounted on the output shaft thereof, or two eccentric masses mounted on its output shaft from two sides of it, or configured to impart a reciprocating motion to the vibration-generating mass, for example, it comprises a coil element with a movable ferromagnetic core. The vibrator can be installed into the stimulating member, into the zone of connection of the first member and the second member, into the first member, into the second member, into the handle of the massage device, single or serially and can be made both built-in and detachable. Additionally, the massager can be made for movement, for example motorized bending, heating of the surface, with a video camera, with a microphone, with a light or audible means of control indication, capable of controlling over a Radio channel (Bluetooth), with the ability of communication and transmission of data with a smart phone and the Internet, with the ability of setting and storing modes of operation, with the ability of electric stimulation, with the possibility of vacuum stimulation. The massager, or its parts, can be made of materials suitable for contact with the skin and mucous membranes, both monolithic and assembled, as well as showerproof and waterproof, with a simple shape consisting of primitive geometric figures, anatomically simulating body parts, or combinations thereof. The surface of the massager can be smoothed, or with a developed relief structure, which comprises protrusions and/or recesses, matte, glossy or with their combination, closed. In order to provide power, the massager is supplied with a detachable (replaceable) or built-in rechargeable power source (hereinafter—battery), for example, a lithium-ion power source, which is electrically connected to the control means, the vibrator and other components of the device. The battery is configured to be charged by connecting to an external power supply via a USB connector with a USB cable, via external electrical contacts, including made of an electrically conductive, elastically deformable material, or electrically conductive portions of the surface, and may be charged by an inductive method in a non-contact manner, and have a stand with a function of a charging device.

The task and technical result of the method of using of the invention is the use of a device for simultaneous affect to two parts of the body, providing an increase in the area of affect to one of them by a distance approximately equal to the length of the vagina. Additional objects and technical results are: an increase in the area of the clitoris that is accessible for stimulation and a static pressing without shifting the flattened stimulating surface in the clitoris while simultaneously reciprocating and simulating the friction stage of the coitus in the vagina so that the distance of movement of the elongated member approximately corresponds to the length of the vagina, while the stimulation of the clitoris should begin in the first position until the vaginal member is inserted into the vagina, continue until it is inserted the full length of the vagina to a second position, and during the return movement vaginal member to the first position where the ends stimulating cycle; providing the ability to stimulate the vagina at various angles and their combination with continuous stimulation of the clitoris; providing multidirectional friction of the vagina and clitoris.

The above technical result is achieved by a method of massage of the genitals, in which a simultaneous massage affect is applied to the first and second parts of the body, using the claimed device, and in the first stage, the first surface portion is placed on the first body portion, and the second surface portion is placed on the second body portion. Then perform translational movement by sliding the first surface portion along the first body portion to the required distance to the second stage, in which the second member is unbent, and the substantially the flexible surface portion is shaped into the first body portion. Then, perform a reverse translational movement by sliding the first surface portion along the first body portion to the required distance, and the cycle is repeated, thus performing a reciprocal movement by sliding the first surface portion along the first body portion to the required distance, including the approximate length of the vagina. In this case, the stimulating member continuously affects on the second body portion, including combining a various range of the mentioned distance. Additionally, the method of massage is characterized by a lubricant is applied to the said surface portions and/or the said body portions and impart the translational movement to the claimed device by holding the first member or connecting it to the body of the user or partner or to a mechanical device, wherein the user may not to apply a lubricant on the second surface portion and thereby prevent the sliding of the second surface portion on the second body portion.

The task and technical result of the method of manufacturing the invention is to obtain a device for simultaneous affect on two parts of the body, providing an increase in the area of affect to one of them by a distance approximately equal to the length of the vagina.

The above technical result is achieved by a method of manufacturing a device for massage of genital organs, at which the claimed device is obtained by using of technological operations. Additionally, the method of manufacturing the device for massaging is characterized by the members of the device for massaging are made as a single whole of silicone rubber with a hardness of 5 units. up to 80 units, preferably 40 units, Shore A, by hot vulcanization in the mold, then the first elongated member is provided with a rigid core, a means for creating mechanical vibrations is installed in the connection zone of the first elongated member and the second elongated member, and means for creating mechanical vibrations in the stimulating member and the power supply and control members in the second end of the first elongated member, or these components are pre-placed in the mold, after which it is filled with silicone rubber and vulcanized using elevated temperature and pressure.

BRIEF DESCRIPTION OF THE DRAWINGS

FIG. 2 is a side view of the device for massage of the second modification in the final stage of insertion into the vagina.

The invention will now be described with reference to specific examples. It should be understood that the following examples are intended to describe embodiments of the invention and are not intended to limit the invention in any way.

DETAILED DESCRIPTION

Figure 1:
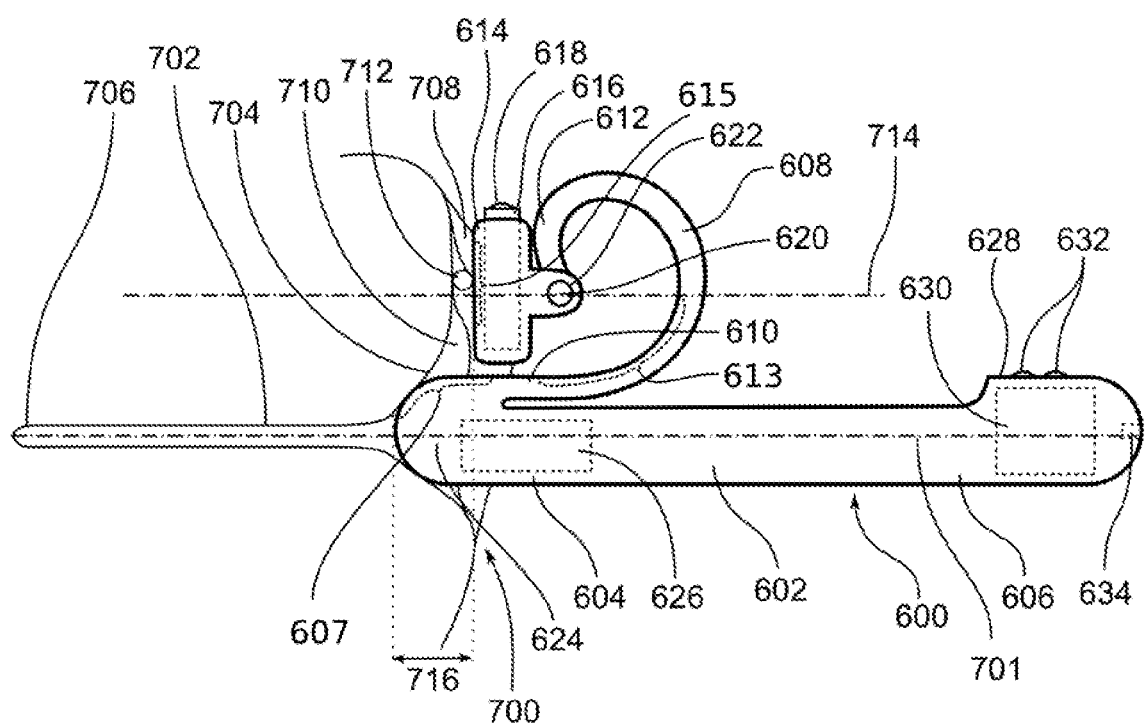
FIG. 1 Side view of the device for massage of the first modification in the initial stage of insertion into the vagina.
Figure 2:
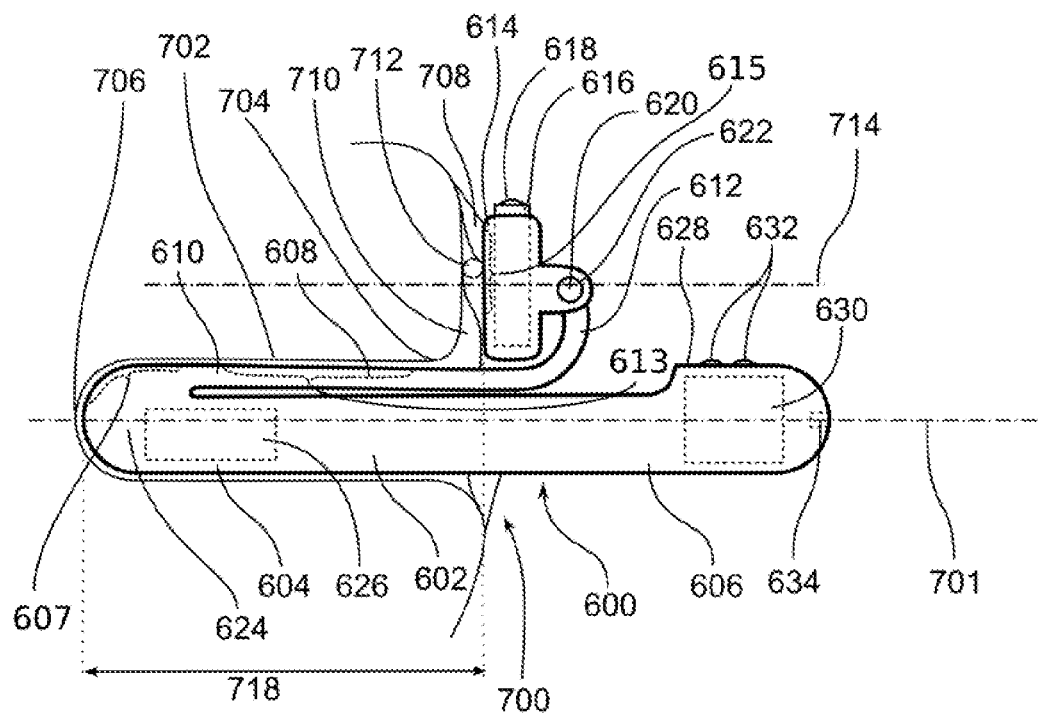
FIG. 2 Side view of the device for massage of the first modification in the final stage of insertion into the vagina.

The implementation of the invention by the example of the first modification of the device. FIG. 1 shows a massage device 600, with a first elongated member 602 made rectilinear, with its first end 604, second end 606 and first surface portion 607. A second elongated member 608, made with curvilinear bending in a spiral, with a first end 610, a second end 612 and a flexible surface portion 613, movably connected to a stimulating member 614 comprising a second surface portion 615 and an attachable vibrator 616 with a control button 618, for which the second the end of the second member contains an axis 620 on which the stimulating member 614 is mounted by means of a hole 622. The connection of the first member and the second member 624 forms a convex rounded distal end of the device, inside of which a vibrator 626 is located. The second end of the first member 606 enters a handle 628, in which a power and control unit 630 is located, with power/speed control buttons and modes 632. At the back of the device is a connector for connecting a charger 634. In the initial stage of insertion, or the first position, the massager 600 is placed in the genital area of the woman 700 in the direction of translational sliding 701 in the direction of the vagina 702 and is inserted into the entrance of the vagina 704 towards the posterior vaginal fornix 706. In this case, the stimulating member 614 by the second surface 615 is located in the clitoral region 708 longitudinally to the labia 710 and abuts against the head of the clitoris 712. A direction of insertion of the first and second members 701 and a direction of movement of the stimulating member 714, as well as the initial distance 716 between the starting point of the stimulation surface and the farthest point of the connection 624 are schematically shown. FIG. 2 shows the same massage device 600 in the final insertion stage, or a second position in which the connection of the members 624 moves along the axis of insertion 701 into the vagina 702 by pushing the first member 602 while holding the device 600 by the handle 628 by a hand of a user or partner. Under the influence of external force, the stimulating member 614 abuts against the clitoris region 708 and contacts the clitoris head 712 with the second surface portion 615, while elastically pushing the second end 612 of the second member 608, which elastically unbends along the first member 602 and, approaching it, forms it is a form, essentially a dildo, suitable for insertion and movement into the vagina. In this case, the flexible surface portion 613 takes a rectilinear shape and, following the first surface section 607, moves into the vagina. The spiral that forms the second member deforms as the device moves, while the stimulating member 614 rotates along the axis 620 relative to the second end 612 of the second member 608, which elastically presses it against the clitoral region 708 thereby providing continuous contact. By reducing the length of the spiral and turning its axis, the axis of rotation 620 of the stimulating member 614 is shifted in the direction of movement 714 essentially parallel to the direction of insertion 701 and synchronously with it by the same distance of insertion. During the complete insertion of the connection of the ends 624 with the first surface portion 607, the stimulating member 614 makes a linear movement in the direction of movement 714 with a slight displacement relative to the direction of insertion 701. In this case, the useful insertion distance, at which simultaneous friction stimulation of the vagina and the clitoris occurs, is the difference between the final distance 718 and the initial distance 716 (FIG. 1). The user sets the required insertion depth of the device 600, thereby affecting the amplitude of the reciprocating movements. When the connection of the ends 624 reaches the fornices of the vagina 706, the user gives the device the reverse movement, in which the elasticity of the second member 608, returning to its original position, provides pressing force to the stimulating member 614 toward the clitoris region 708 and the clitoris head 712 by the second surface portion 615. Additionally, the user has access to vibration functions, both in the vagina and in the clitoris, and their speed, operating modes and combination are selected by pressing buttons 618 and 632.

Figure 3:
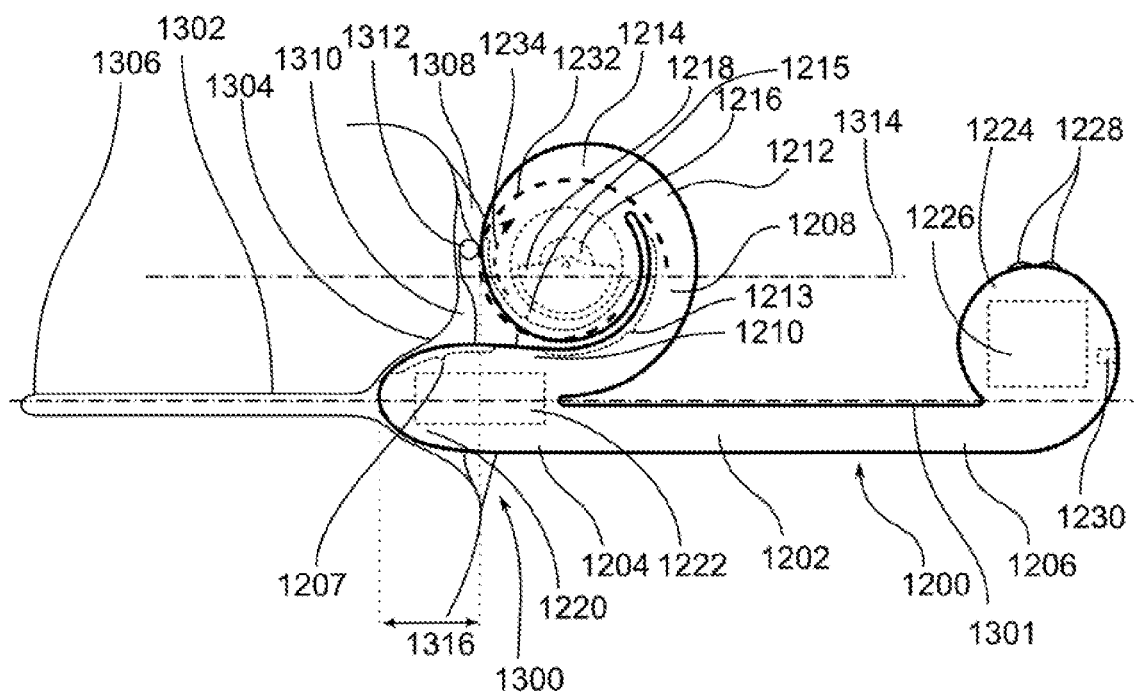
FIG. 3 is side view of the device for massage of the second modification in the initial stage of insertion into the vagina.
Figure 4:
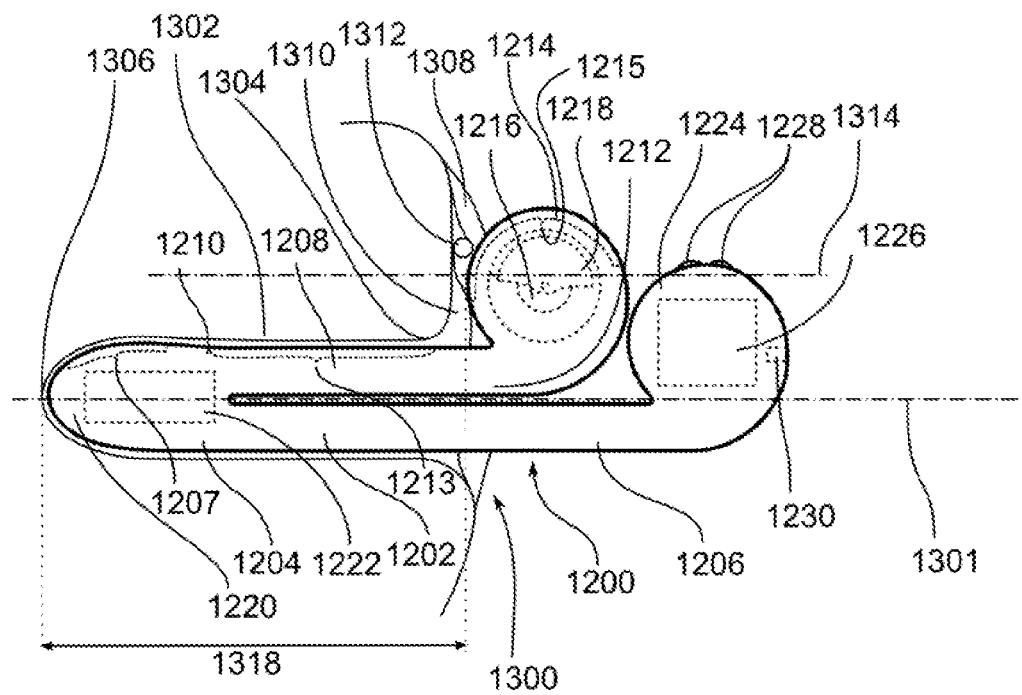

The implementation of the invention by the example of the second modification of the device. FIG. 3 shows a massage device 1200, with a first elongated member 1202 made rectilinear, with its first end 1204, second end 1206 and a first surface portion 1207. A second elongated member 1208 having approximately the same thickness and cross section as the first member made with curvilinear bending in arc, with a first end 1210, a second end 1212 and a flexible surface portion 1213, and the second end 1212 is connected with a smooth transition in a stimulating member 1214 made in the shape of a body of revolution, comprising a second surface section 1215, with a transversely mounted non-removable powerful vibrator 1216, with an enlarged eccentric mass 1218 mounted on its output shaft. The first end of the first member forms a convex rounded front end of the device 1220, within which a vibrator 1222 is located. The second end of the first member 1206 transitions into a rounded handle 1224, in which a power supply and control unit 1226 is located, with an on/speed control buttons and vibration modes 1228. A connector 1230 for connecting a charging device is disposed at the rear end of the device. In the initial stage of insertion, or in the first position, the massager 1200 is located in a genital area of the woman 1300 in a direction of insertion 1301 towards a vagina 1302 and is inserted into an entrance to the vagina 1304 so that the first surface portion 1207 affects on the first human body portion, which is the front the wall of the vagina 1302, towards its posterior vaginal fornix 1306. In this case, the stimulating member 1214 is located in the clitoral region 1308 along to the labia 1310 and abuts against the head of the clitoris 1312 with the second surface portion 1215. Schematically shown is a direction of translational sliding 1301 of the first surface portion 1207 and a direction of movement 1314 of the stimulating member 1214, as well as the initial distance 1316 between the starting point of the second surface portion and the most distant point of the distal end of the device 1220. Schematically shows an intermediate position 1232 of the stimulating member 1214 and a direction of rotational sliding 1234 when sliding the first surface portion 1207. FIG. 4 shows the same massage device in the final stage of insertion, or in the second position, in which the first surface portion 1207 moves along the insertion direction 1301 into the vagina 1302 by pushing the first member 1202 while holding the device 1200 by the handle 1224 by the hand of a user or partner. In this case, the stimulating member 1214 abuts against the clitoral region 1308 and the head of the clitoris 1312 with the second surface portion 1215 and elastically pushes the second end 1212 of the second member 1208, which elastically unfolds along the first member 1202 and, approaching it, forms an essentially dildo shape suitable for insertion and movement by sliding into the vagina. In this case, the flexible surface portion 1213 takes a rectilinear shape and, following the first surface portion 1207, moves into the vagina. The arc of the second member 1208 is unwind as the device moves and facing toward to the clitoral region 1308 the convex round second surface portion 1215 of the stimulating member 1214 is rotary moved by sliding along the head of the clitoris 1312 making continuous contact and friction stimulation by friction. During the complete insertion of the distal end 1220, the stimulating member 1214 rotates about an approximately unfolded angle relative to the axis of movement 1314 with a slight displacement relative to the direction of insertion 1301. In this case, the useful insertion distance, at which simultaneous friction stimulation of the vagina and the clitoris occurs, is the difference between the final distance 1318 and the initial distance 1316 (FIG. 3). The user set up the required distance of the depth of insertion of the device 1200 and the amplitude of its movement, while affecting the amplitude and duration of the rotates back and forth movements of the stimulating member 1214. When the connection of the ends 1220 reaches the fornices of the vagina 1306, the user gives the device the reverse movement, in which the elasticity of the second member 1208 provides the stimulating member 1214 to rotate in the opposite direction and returns it to its original position, while providing pressing force to the stimulating member 1214 to the clitoral region 1308 and to the head of the clitoris 1312. Additionally, the user has access to vibration functions, both in the vagina and in the clitoris, and their speed, operating modes and combination are selected by pressing buttons 1228.

Figure 5:
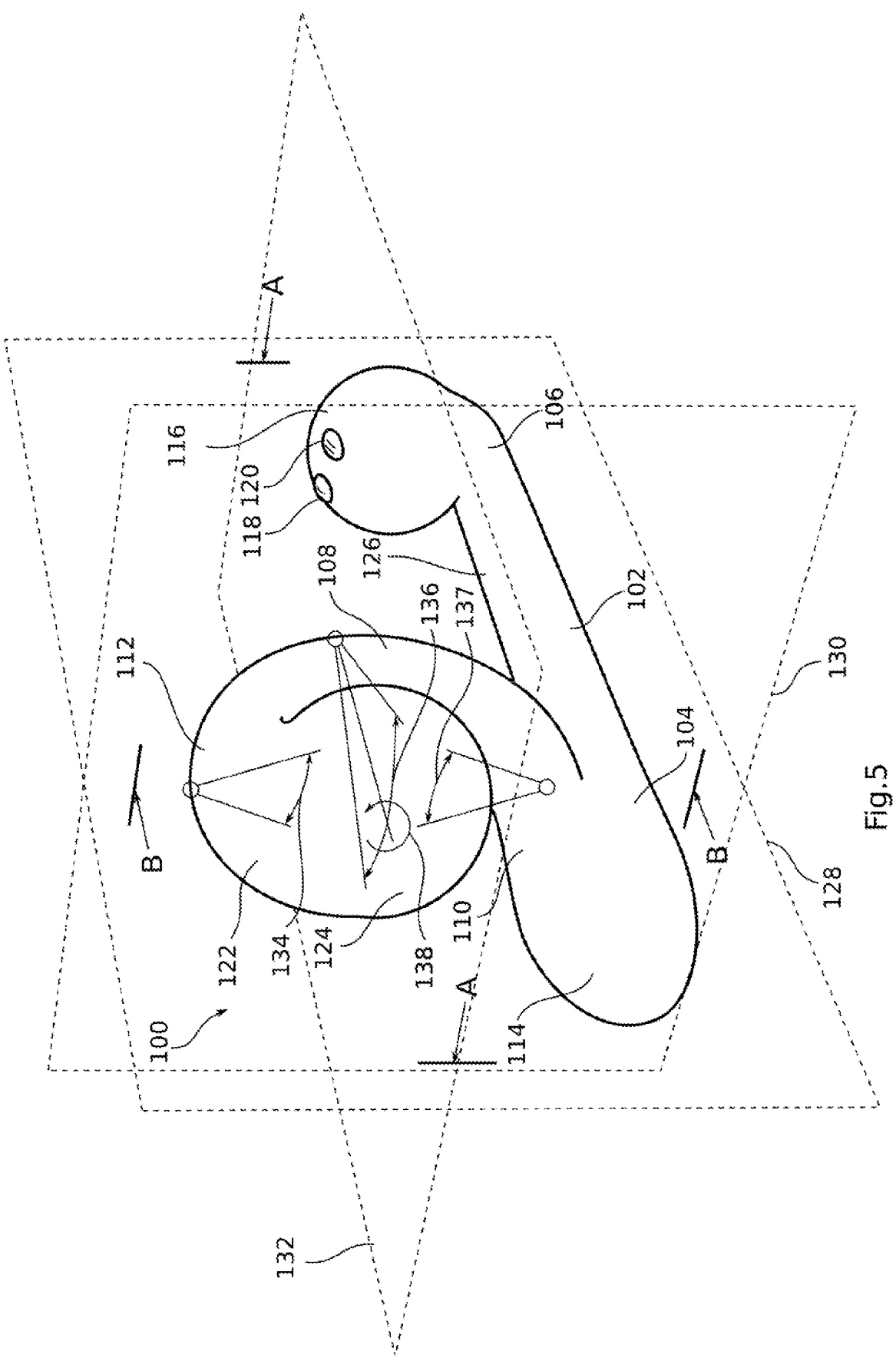
FIG. 5 is a perspective view of the device for massage of the third modification.

The implementation of the invention by the example of the third modification of the device. FIG. 5 shows a perspective view of a massage device 100 comprising a first member 102 with a first end 104 and a second end 106, and a second member 108 with an arcuate bend, with a first end 110 and a second end 112. The first member and the second member are connected by their first ends to form a rounded member 114. The second end of the first member is connected to a spherical handle 116 comprising control buttons 118 and 120, and the second end of the second member 112 is connected to a spherical stimulating member 122 comprising a stimulating surface 124 extending from the outer to the inner surface of the second end 112. The device is made with a monolithic closed surface 126 of silicone rubber.

Figure 6:
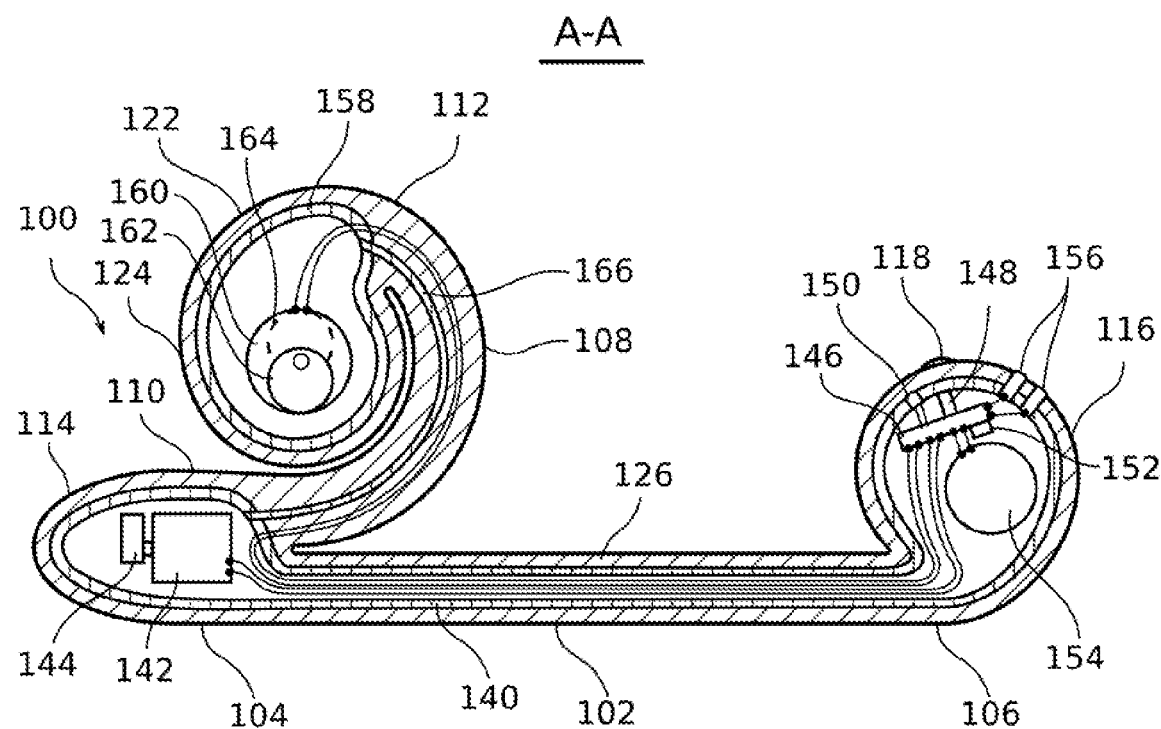
FIG. 6 is a longitudinal section of the device for massage in FIG. 5.
Figure 7:
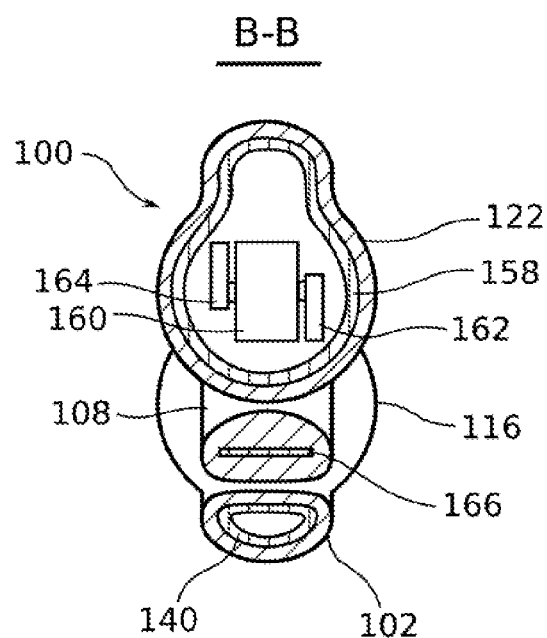
FIG. 7 is a cross-sectional view of the massage device in FIG. 5.
Figure 8:
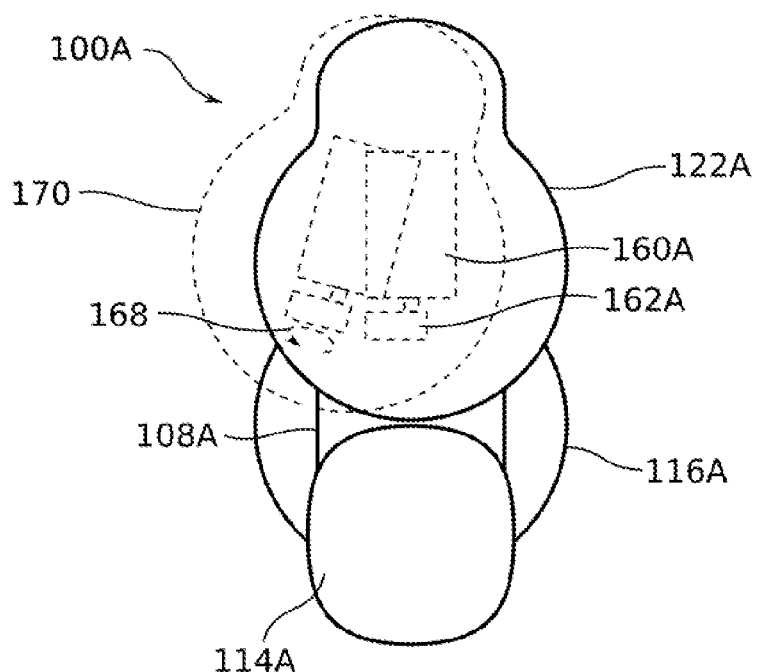
FIG. 8 is a front view of the modification of the massage device in FIG. 5 with a right displacement of the stimulating member.
Figure 9:
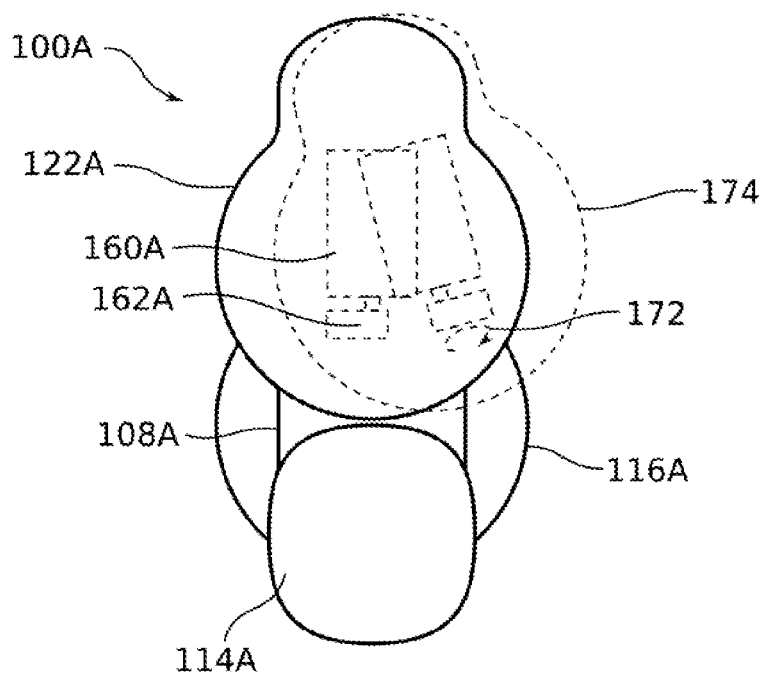
FIG. 9 is a front view of the modification of the massage device in FIG. 5 with a left displacement of the stimulating member.

Schematically shows a bending plane of the second member or a longitudinal vertical plane (hereinafter the first plane) 128, transverse to it and the first member or a transverse vertical plane (hereinafter the second plane) 130, and transverse to it and longitudinal to the first member or longitudinal horizontal plane (hereinafter the third plane) 132. The arrows show a first direction 134 of a displacement or swing of the stimulating member, for example, when installing a vibrating motor with one eccentric or a linear vibrator in the stimulating member, a second direction 136, for example, when installing at the intersection of the second and third plane of a vibrating motor with two eccentrics with shifted phases or a linear vibrator, a third direction 137 shows the displacement of the second member containing a linear vibrator in the second plane and not containing an elastic strip, the fourth or orbital direction of 138, for example when installing a vibration motor with an eccentric with a rotation in the first plane. FIG. 6 shows a longitudinal cross-sectional view A-A of FIG. 13, which further shows a first housing 140 located in the first member 102 from the connection of the first ends 114 to the handle 116, which contains a first electric motor 142 with the first eccentric 144, a printed circuit board (PCB) of control means 146 with a rod 148 of elastically pressed button 118, an LED 150, a radio control unit 152 and a battery 154, and contacts 156 of electrically conductive elastically deformable material for charging the power supply means. A second housing 158 housed in the stimulating member 122 comprises a second motor 160 with a first eccentric 162 and a second eccentric 164. The first and second housing are covered with silicone rubber, and the second member is completely made of it and contains an elastic arcuate metal strip 166 connecting the first and second housing. FIG. 7 shows a cross-sectional view B-B, which further shows the location of the eccentric 162 with a phase angle offset by 180 degrees relative to the second eccentric 164. The electrical connection of the vibration, control and power supply means is schematically indicated. The device is placed in a first position so that the connection of the first ends 114 is located in a vaginal area, and the stimulating member 122 is pressed against a clitoris by the surface 124. Using the buttons 118 and 120, a user controls the first electric motor 142 and the second electric motor 160, respectively. To charge the battery 154, the user connects an external current source from USB or a charger to the contacts 156, the microprocessor of the control means 146 determines the polarity of the connected contacts, and directs the current to the required polarity to the battery. FIG. 8 shows a front view of a modified device 100A, with the connection of a first ends 114A of a first member and a second member 108A with a handle 116A. The difference is that the vibration motor 160A is installed in the stimulating member 122A with one eccentric 162A, when rotating in the direction 168, the stimulating member is moved to position 170, and when rotating in the direction 172, to position 174 (FIG. 9).

Figure 10:
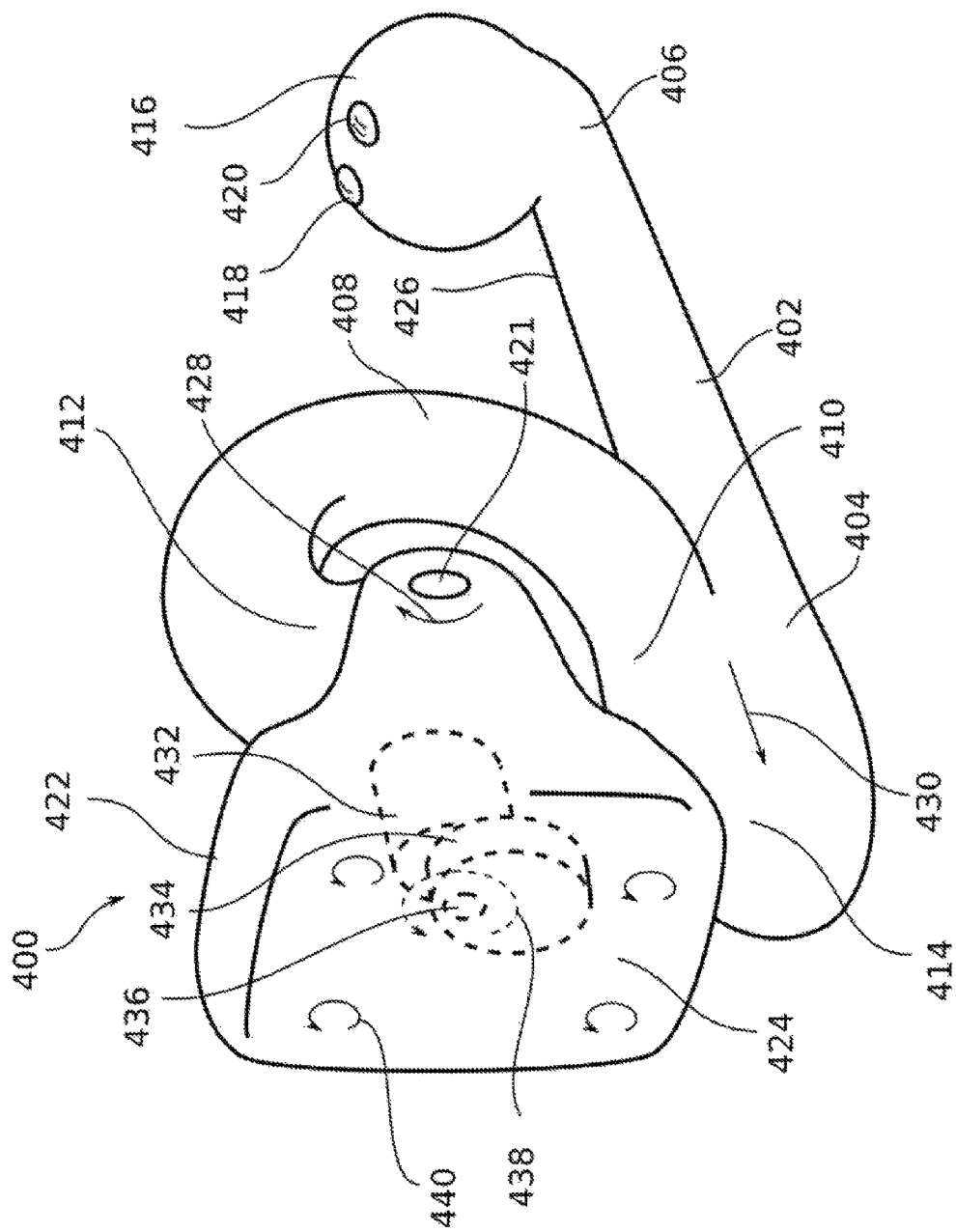
FIG. 10 is a perspective view of the device for massage of the fourth modification.

The implementation of the invention by the example of the fourth modification of the device. FIG. 10 shows a perspective view of the massage device 400, comprising a first member 402 with a first end 404 and a second end 406, and a second member 408 of silicone rubber with a spiral bend, with a first end 410 and a second end 412. The first member and the second member are connected by their first ends to form a rounded member 414 into which a vibrator is mounted. The second end of the first member is connected to a spherical handle 416 comprising control buttons 418 and 420, and the second end of the second member 412 on an axis 421 is movably and electrically connected to the stimulating member 422 containing a flattened stimulating surface 424 that is extended forwardly relative to the connection 414. The device is made with a surface 426 of silicone rubber. A direction 428 of rotation of the second end 412 of the second member relative to the stimulation member 422 is schematically shown as it moves along the first member 402 from a first position in which the stimulation member 422 is moved closer to the first end 404 of the first member and a second position in which it is brought closer to the second end 406 of the first member when the connection 414 is inserted into the vagina in the direction 430 and the surface 424 abuts against the clitoral region. The stimulating member comprises an electric motor 432 with an eccentric mass 434 mounted on a shaft 436, the axis of which is essentially parallel to the direction 430. The direction of rotation 438 of the eccentric mass 434 and the generating orbital displacements 440 of the surface 424 on the clitoral region are shown schematically.

Implementation of a method of application of the invention in an example of use of the fourth modification shown in FIG. 10. The user applies a lubricant to the device 400 and genital organs, presses the stimulating member 422 with the surface 424 to the clitoral region and places the connection 414 of the first ends of the first and second members opposite the entrance to the vagina and sets the device in the first position. Using the control button 418, the user controls the actuation and mode of operation of the electric motor 432, which drives the eccentric mass 434, which generates vibrations of the stimulating member 422 and thereby displaces the surface 424 along a closed path in circular rubbing movements along the clitoral region. Using the control button 420, the user controls the actuation and mode operation of the vibrator installed in the connection 414 for massage effects of vibration on the vagina. Holding the device 400 by the handle 416, the user inserts the connection 414 into the entrance to the vagina and pushes the first member 402 into the vagina, which due to the connection 414, pulls the first end 410 of the second member 408 under the influence of which, as well as the abutment of its second end 412 through the connection with the stimulating member 422 to the clitoris, the second member 408 unbends along the first member 402 so that they come together and form a shape suitable for insertion and rubbing of the vagina, and thereby presses the stimulating member 422 against the clitoris, the second end 412 being rotated about the axis 421 relative to the stimulating member 422, and sets the device to the second position. When the connection 414 is pulled out of the vagina by the handle 416, the second member 408 returns to its original shape and thereby presses the stimulating member 422 to the clitoris, so that the user may not completely withdraw the connection 414 from the vagina completely or combine these stimulation options, so that the stimulating member 422 is continuously pressed against the clitoris during the reciprocating movements of the first member 402. By repeating these manipulations, the user thereby performs reciprocating vaginal stimulation, and the depth and amplitude of the stimulation can be changed arbitrarily, combining short and long movements in different parts of the vagina, while simultaneously stimulating the clitoris. In addition, the user can stimulate the vagina at various angles, for example from bottom to top, to stimulate the "G-spot", or from top to bottom, or along the body, as well as combine these movements while maintaining continuous contact of the stimulating member with the clitoris.

The implementation of the method of applying the second embodiment of the device using the third modification as an example. The user applies a lubricant to the device 100 and genitals, inserts the connection 114 of the first ends of the first and second member into the entrance to the vagina and presses the stimulating member 122 with the surface 124 to the clitoris region and sets the device in the first position. Using the control button 118, the user controls the actuation and mode operation of the electric motor 142 mounted in the connection 114 for massage action by vibration on the vagina. Using the control button 120, the user controls the turning on and mode operation of the electric motor 160, which drives the eccentric masses 162 and 164, which generate vibrations of the stimulating member 122 and thereby displace surface 124 along a closed path by rubbing movements along the clitoris area. Holding the device 100 by the handle 116, the user inserts the connection 114 into the entrance to the vagina and pushes the first member 102 into the vagina, which due to the connection 114, pulls the first end 110 of the second member 108 under the action of which, as well as the abutment of its second end 112 through the connection with the stimulating member 122 to the clitoral region, the second member 108 unbends along the first member 102 so as to approach together and form a shape suitable for insertion and rubbing of the vagina, and thereby presses the stimulating member 122 against the clitoris, the stimulating member 122 being rotated about an axis approximately coincident with the axis of the motor 160 and its surface 124 thereof being pivotally moved on clitoral region toward the entrance to the vagina, the clitoris that is felt as friction in the opposite direction, i.e., from the inside out, affecting a massage effect by rubbing, and sets the device in the second position. When the connection 114 is pulled out of the vagina by the handle 116, the second member 108 returns to its original shape and thereby presses and rotates the stimulating member 122 along the clitoral region, while the stimulating member 122 is continuously pressed against the clitoral region during the reciprocating movements of the first member 102. By repeating these manipulations, the user thereby performs reciprocating vaginal stimulation, and the depth and amplitude of the stimulation can be changed arbitrarily, combining short and long movements in different parts of the vagina, and synchronous reciprocation of the clitoris and clitoris. And also, slightly unbending the second member, the user places the stimulating member 122 on the clitoral region without the use of lubricant, so that he makes rocking movements along the first plane 128 without sliding along the clitoral region with linear movement of the first member with a short amplitude. In addition, the user can stimulate the vagina at various angles, for example from bottom to top, to stimulate the "G-spot", or from top to bottom, or along the body, as well as combine these movements while maintaining continuous contact of the stimulating member with the clitoris.

Figure 11:
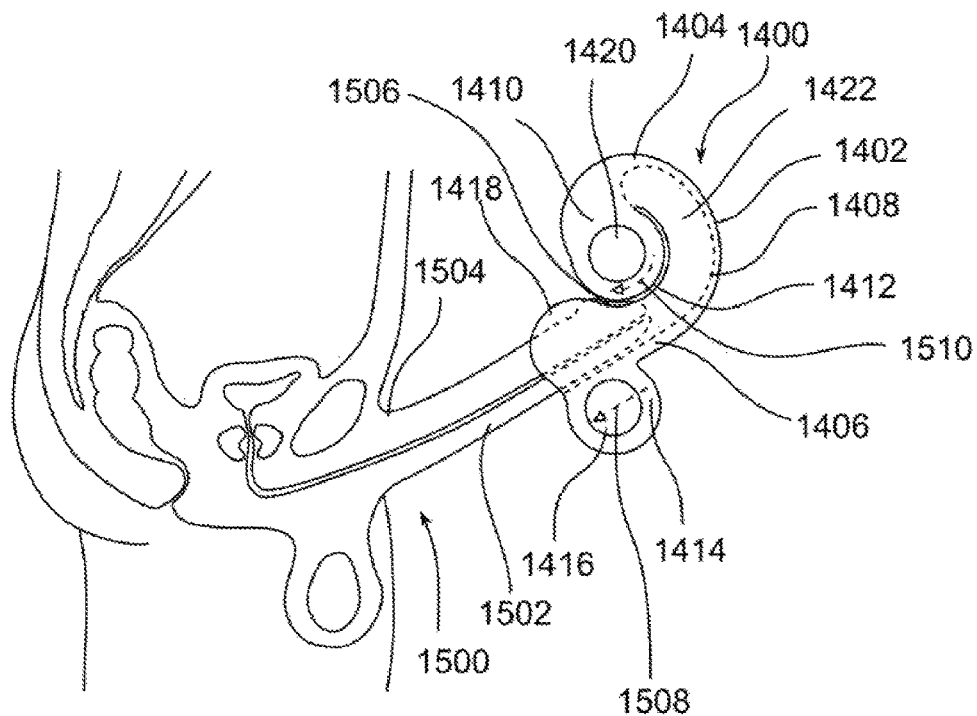
FIG. 11 is a side view of the device for massage of the fifth modification in the initial stage of movement along the penis.
Figure 12:
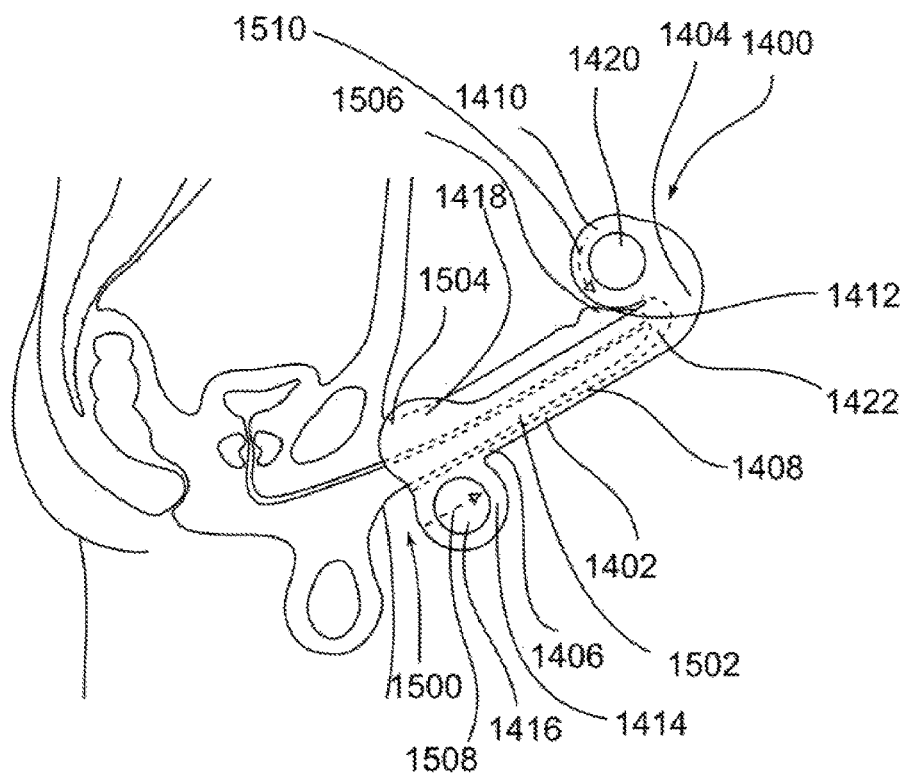
FIG. 12 is a side view of the device for massage of the fifth modification in the final stage of movement along the penis.

The implementation of the invention by the example of the fifth modification of the device. FIG. 11 shows a device for massaging genital organs 1400 with a first elongated arcuate member 1402 with a first end 1404 and a second end 1406 and a first surface portion 1408. The first end 1404 is connected to the second member 1410 with a second surface portion 1412. The second end 1406 is connected to an additional U-shaped member 1414 containing a vibrator 1416 and wing-shaped elements bent inward 1418. The second member contains a vibrator 1420. The first member is made with a U-shaped longitudinal recess 1422, schematically shown by a dashed line. At the initial stage of use, the device 1400 is put on genital organs 1500, on the shaft of the penis 1502 towards its base 1504 so that the head of the penis 1502 contacts on the one hand the second surface portion 1412 of the second member 1410, and on the other hand contacts the first surface portion of the first member 1402 and is placed in a U-shaped recess 1422. The user holds the device by an additional member 1414 and moves it along the shaft of the penis 1502 towards the base 1504. The direction of movement of the first member 1508 and the direction of rotation of the second member 1510 are conventionally shown. FIG. 14 shows the same device in the final stage of use, in which the first member 1402 is unfolded and the first portion of the surface 1408 takes the shape of an erect penis. Additional member 1414 shifting toward the base of the penis 1504, and the wing members 1418 hold and direct the movement of the device along the penis. At the same time, the second portion of the surface 1412 is pressed against the head of the penis and rotates along it, providing interaction, as well as the first portion of the surface 1408 interacts with the penis shaft.

The implementation of the invention is not limited to the description, but is considered based on the understanding of the prior art by a person skilled in the art, including indications of all the necessary electromechanical parts of the device, printed circuit boards, microprocessors, communications, software, as well as functional connections between the components of the device. These embodiments of the invention are preferred and do not limit its implementation, any modifications and improvements should be considered within the scope of protection of the invention. The terminology used herein is intended to describe specific embodiments and is not intended to limit the present invention. Used in the present description, the singular can also be used to include the plural, unless the context clearly indicates otherwise. The terms "contains" and/or "comprising" used in this description indicate the presence of these signs, their units, steps, operations, members and/or components, but does not exclude the presence or addition of one or more other signs, their units, stages, operations, members, components and/or groups thereof. Any combinations of technical solutions, features, elements and means listed above can be embodied in one device depending on the possibility of their combination, and a description of their combinations in one device is advisory in nature, not limiting their implementation in another device of the same purpose.

Obviously, the above embodiments are examples and can be modified in many ways. Such present or future changes should not be construed as a departure from the essence and scope of the invention, and all such modifications, as will be readily understood by a person skilled in the art, are intended to be included in the scope of the following claims. A person skilled in the art will understand that other massager designs for two zones with an unfolding member can be considered without departing from the general scope of the essence of the present disclosure.

The invention claimed is:

1. A device for massaging genital organs, comprising:
a first member,
a second member and
a stimulating member,
    the first member comprising a first surface portion configured to affect a first human body portion, the first member is made elongated, having a first end and a second end,
    the second member is made elongated and connected by its first end to the first end of the first member, and connected by its second end to the stimulating member,
    the stimulating member comprises a second surface portion configured to affect a second human body portion, wherein the first surface portion is configured to translationally slide along the first human body portion, and the second surface portion is configured to press against the second human body portion during the translational sliding, wherein the second member is configured with a curvilinear bend forming an arc along a bending plane of the second member, and configured to elastically unbend along the first member and thereby move the stimulating member from a first position in which the second surface portion is closer to the first end of the first member, to a second position in which the second surface portion is distant from the first end of the first member, the second member is configured to elastically unbend during the translational sliding and thereby move the stimulating member in an opposite direction of a direction of the translational sliding and is configured to press the second surface portion to the second human body portion in the process of the translational sliding, wherein the second surface portion is a stimulating surface formed in an arc that coincides with the arc formed from the curvilinear bend of the second member, and the stimulating surface is configured to face the first end of the second member during the translational sliding, wherein the second member is made of an elastically deformable material, and contains a flexible surface portion configured to transform from a curvilinear shape into a rectilinear shape during the translational sliding.

2. The device of claim 1, further comprising an affecting means comprising at least one stimulation means, comprising a vibration means configured to impart reciprocating movement to a vibration-generating mass comprising a coil member with a movable ferromagnetic core, at least one electric current source comprising a lithium-ion battery adapted for charging by at least one contact made from electrically conductive and elastically deformable material, and at least one control means configured to control the stimulation means, comprising a variety of settings, a plurality of buttons configured to be elastically pressed, light indication, and further including means for remotely controlling the stimulation means.

3. The device of claim 1, wherein the stimulating member comprises at least one vibrational means configured to prevent lateral displacement of the stimulating member relative to the bending plane of the second member while generating vibration, wherein the stimulating member is configured to generate vibration using an electric motor mounted transversely to the bending plane of the second member with an eccentric mass mounted on it, wherein the rotation plane of the eccentric mass coincides with the bending plane of the second member.

4. The device of claim 1, wherein the second member is configured to prevent lateral displacement of the stimulating member relative to the bending plane of the second member, by having a transverse cross-section that is elongated across the bending plane, and/or by having an elastic strip of spring metal mounted on a widest side of the second member transverse to the bending plane which provides longitudinal deformation and prevents transverse deformation, and has an approximate ratio of width to thickness of 50:1.

5. The device of claim 1, wherein the stimulating member is elastically suspended relative to the first member, and is capable of lateral elastic deflection relative to the first member, and wherein the stimulating member further comprises a vibration means configured for generating angular oscillations using an electric motor with an output shaft on two sides thereof on which two eccentric masses are respectively mounted, and wherein phase angles of the two eccentric masses are rotated relative to each other along an axis of the output shaft by 180 degrees, with an oscillation plane transverse to the bending plane of the second member, or coinciding with the bending plane.

6. The device of claim 1, wherein the device is made showerproof or waterproof by providing each of the first member, a connection of the first member and the second member, the second member, and the stimulating member with a surface of silicone rubber, either made monolithically of said silicone rubber, or covered with said silicone rubber, wherein the device surface is made smooth, or with a developed relief structure, comprising protrusions configured for enhanced stimulation of a G-spot.

7. The device of claim 1, wherein the first surface portion is configured to provide a massaging affect, including friction and vibration, on the first human body portion which further comprises a human cavity, and the second surface portion is configured to provide a massaging affect, including friction and vibration, on the second human body portion which is an adjacent portion of the first human body portion, wherein the first human body portion comprises a front wall of a vagina, and the second human body portion comprises a head of a clitoris, or wherein the first human body portion comprises an anus, and the second human body portion comprises a crotch, and the flexible surface portion is configured to unbend during translation sliding along the first human body portion, and is thereby configured to form an inverse shape of the first human body portion, wherein the second member is made of an elastomer.

8. The device of claim 7, wherein the first member is made elongated, with the first end connected to the first end of the second member in the direction of the first member, so that the curvilinear bend of the second member is directed away from the first member, and the first end of the first member is configured to be inserted jointly with the first end of the second member into the vagina, and further comprises an electric means configured to affect the first human body portion or the second human body portion, and the second end of the first member includes a handle, and contains an electric current source and a control means, wherein the first member comprises a rectilinear shape, or is made with a slight arcuate bend in the bending plane of the second member, wherein the first member further includes a rigid portion in a direction of the first end of the second member, along which the second member is configured to unbend, and thereby form a shape of an erect penis and move the stimulating member along the rigid portion from the first position in which the stimulating member is brought closer to the first end of the first member, to the second position in which the stimulating member is close to the second end of the first member, wherein the movement of the stimulating member from the first position to the second position occurs at a distance approximately equal to a length of the vagina.

9. The device of claim 1, wherein the first surface portion is configured to provide a massaging affect, in particular friction and vibration, on a shaft of a penis, and the second surface portion is configured to provide a massaging affect, including friction and vibration, on a head of the penis, the flexible surface portion is configured to unbend during the translation sliding along the first human body portion, and thus is configured to take a shape of an inverse form of the first human body portion, wherein the second member is made of an elastomer.

10. The device of claim 1, wherein the stimulating member is elastically connected to the second end of the second member, and is made rounded and convex in the bending plane of the second member, wherein the second surface portion is configured to provide massaging affects via pressure and rubbing on the second human body portion, and is configured for rotational sliding on the second human body portion in the bending plane of the second member in a direction from the first human body portion during transformation from the first position to the second position due to a pushing force of the second human body portion on the stimulating member in the opposite direction of the translational sliding when the second surface part is pressed into the second human body portion, and towards the first human body portion during transformation from said second position to said first position due to the pushing force of the second member on the stimulating member in the direction of said translational sliding during restoration of the second member to its original shape, wherein a length of an arc of the rotational sliding is approximately equal to a length of a vagina, wherein the first member is configured to be held by a hand and to impart reciprocating sliding to the first member with the first surface portion over the first human body portion, and the second member is configured to impart to the stimulating member rotational sliding of the second surface portion along the second human body portion, and the second member is continuous with the second surface portion, so that centers of their respective arcs are coincident, and the second member's arc partially envelopes a second surface portion.

11. The device according to claim 10, wherein the first member and the second member have a semicircular cross-section with fillets between an arc and a chord of approximately the same size, with a height of approximately 16 mm, and a width of approximately 30 mm, and/or when approaching, their cross sections form a circle, the first member, the second member, and the stimulating member are integrally formed and/or smoothly connected to each other, connection of the first member and the second member is made end-face and forms a distal end of the device, the connection of the first member and the second member is made round and contains a vibration means, the stimulating member is made in the form of a body of revolution with a stimulating surface formed in an arc of approximately 240 degrees circumferentially, with a radius of approximately 25 mm in the bending plane of the second member, with the arc facing towards the connection of the first member and the second member, the curvilinear bend of the second member is approximately 125 degrees circumferentially, with an outer radius of approximately 13 mm, the curvilinear bend of the second member has a single center with said stimulating surface.

12. A method for providing a massaging action of genital organs, characterized by simultaneously performing the massaging action on a first human body portion and a second human body portion,
by using a device comprising:
a first member,
a second member and
a stimulating member,
the first member comprising a first surface portion configured to affect the first human body portion, the first member is made elongated, having a first end and a second end, the second member is made elongated and connected by its first end to the first end of the first member, and connected by its second end to the stimulating member,
the stimulating member comprises a second surface portion configured to affect the second human body portion,
wherein the second member is made with a curvilinear bend forming an arc along a bending plane of the second member, and configured to elastically unbend along the first member, and thereby move the stimulating member,
the second member configured to elastically unbend during translational sliding, and thereby move the stimulating member in an opposite direction of a direction of the translational sliding, and configured to press the second surface portion to the second human body portion in the process of the translational sliding,
wherein the second surface portion is a stimulating surface formed in an arc that coincides with the arc formed from the curvilinear bend of the second member, and the stimulating surface is configured to face the first end of the second member during the translational sliding,
wherein the second member is made of an elastically deformable material, and contains a flexible surface portion configured to transform from a curvilinear shape into a rectilinear shape during the translational sliding,
and further wherein in a first stage the first surface portion is placed on the first human body portion, and the second surface portion is placed on the second human body portion, then the translational sliding occurs by moving the first surface portion along the first human body portion across a required distance that is an approximate length of a user's vagina, to a second stage in which the second member is unbent, and the flexible surface portion is in a shape of the first human body portion, then the translational sliding is reversed by moving the first surface portion along the first human body portion across the required distance, such a cycle being repeated, and thereby making a reciprocal motion by sliding the first surface portion along the first human body portion across the required distance, while the stimulating member continuously affects the second human body portion, and the reciprocal motion includes a combination of various intermediate distances within a range of the user's required distance.

13. The device of claim 1, wherein the stimulating member further comprises an electric means configured to affect a human body, and the device comprises a control means for controlling the electric means, wherein the second member contains flexible electrical conductors that electrically connect the control means with the electric means.

14. A method of manufacturing a device for massaging genital organs by use of hot vulcanization to obtain the device of claim 1.

15. A device for massaging genital organs, comprising:
a first member,
a second member and
a stimulating member,
the first member comprising a first surface portion configured to affect a first human body portion, the first member is made elongated, having a first end and a second end, the second member is made elongated and connected by its first end to the first end of the first member, and connected by its second end to the stimulating member, wherein the stimulating member further comprises a second surface portion configured to affect a second human body portion, wherein the first surface portion is configured to translationally slide along the first human body portion, and the second surface portion is configured to press against the second human body portion during said translational sliding, wherein the second member is made with a curvilinear bend and is configured to elastically unbend along the first member, and thereby move the stimulating member from a first position in which the second surface portion is closer to the first end of the first member, to a second position at which the second surface portion is closer to the second end of the first member, the second member is configured to elastically unbend during translational sliding, and thereby move the stimulating member in an opposite direction of a direction of the translational sliding, and configured to press the second surface portion to the second human body portion in the process of the translational sliding, wherein the stimulating member is movably connected to the second end of the second member with axial rotation in a bending plane of the second member, and is further mechanically and releasably connected to the second end of the second member, wherein the second member is made of an elastically deformable material, and contains a flexible surface portion configured to transform from a curvilinear shape into a rectilinear shape during the translational sliding.

16. The device of claim 15, wherein the stimulating member further comprises an electric means to affect a human body and the device comprising a control means for controlling the electric means, wherein the second member contains flexible electrical conductors that electrically connect the control means with the electric means, wherein a connection of the stimulating member and the second end of the second member provides electrical connection of the electric means with the flexible electrical conductors, and allows axial rotation in the bending plane of the second member, the second member is configured to bend in a spiral, the second end of the second member is configured to move from the first position to the second position parallel to the opposite direction of the translational sliding, wherein the second surface portion is configured to prevent sliding along the second human body portion by having a flattened surface that can be extended forward from the first surface portion, and is configured to provide massage to the second body portion by pressure and by an affecting means, both in the process of the translational sliding and without contact of the first surface portion with the first human body portion.

* * * * *